(12) United States Patent
Changaris et al.

(10) Patent No.: US 12,611,380 B2
(45) **Date of Patent: \*Apr. 28, 2026**

(54) SOLUTION AND METHOD FOR REDUCING THE VIRULENCE OF VIRUSES, BACTERIA, YEASTS, OR FUNGUS

(71) Applicant: David G Changaris, Louisville, KY (US)

(72) Inventors: David G. Changaris, Louisville, KY (US); Anne L. Carenbauer, Louisville, KY (US)

(73) Assignee: David Changaris, Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/530,439

(22) Filed: Nov. 18, 2021

(65) Prior Publication Data

US 2022/0071902 A1 Mar. 10, 2022

Related U.S. Application Data

(63) Continuation of application No. 16/938,753, filed on Jul. 24, 2020, now Pat. No. 11,197,824.

(60) Provisional application No. 63/003,249, filed on Mar. 31, 2020, provisional application No. 62/961,994, filed on Jan. 16, 2020.

(51) Int. Cl.
| | |
|---|---|
| *A61K 9/08* | (2006.01) |
| *A01N 37/06* | (2006.01) |
| *A61K 9/00* | (2006.01) |
| *A61K 31/19* | (2006.01) |

(52) U.S. Cl.
CPC ............... *A61K 9/08* (2013.01); *A01N 37/06* (2013.01); *A61K 31/19* (2013.01); *A61K 9/0014* (2013.01); *A61K 9/0019* (2013.01); *A61K 9/0034* (2013.01); *A61K 9/0043* (2013.01); *A61K 9/0048* (2013.01); *A61K 9/0053* (2013.01); *A61K 9/0082* (2013.01)

(58) Field of Classification Search
CPC ............ A61K 31/231; A61K 9/08; A01P 1/00
See application file for complete search history.

(56) References Cited

U.S. PATENT DOCUMENTS

| | | | | | |
|---|---|---|---|---|---|
| 4,997,851 | A | * | 3/1991 | Isaacs .................... | A61K 31/19 |
| | | | | | 514/552 |
| 9,549,550 | B2 | * | 1/2017 | Changaris .............. | A61K 9/107 |
| 9,962,354 | B2 | * | 5/2018 | Changaris ............ | A61K 9/0014 |
| 2005/0038118 | A1 | * | 2/2005 | O'Shea ................... | A61P 11/00 |
| | | | | | 514/560 |
| 2016/0100577 | A1 | * | 4/2016 | Salminen ............... | A01N 41/04 |
| | | | | | 514/517 |
| 2017/0079945 | A1 | * | 3/2017 | Changaris ............ | A61K 31/201 |

OTHER PUBLICATIONS

Blair et al (F1000 Research, 2016, vol. 5, pp. 1-7) (Year: 2016).*
Boyce (Antimicrobial Resistance and Infection Control, 2016, vol. 5, 1-10) (Year: 2016).*
Ke et al (Communications Chemistry, Apr. 2020, vol. 3, pp. 1-12) (Year: 2020).*
Jang et al (Journal of Applied Microbiology, 2015, vol. 120, pp. 280-288) (Year: 2015).*
Martinez-Fructuoso et al (ACS Infect Dis, 2023, vol. 9, pp. 1245-1256) (Year: 2023).*
Socratic Q&A (What functional groups can act as acids?, downloaded Mar. 2024, https://socratic.org/questions/what-functional-groups-can-act-as-acids) (Year: 2024).*
WHO (Report of the WHO-China Joint Mission on Coronavirus Disease 2019 (COVID-19), Feb. 24, 2020, https://www.who.int/docs/default-source/coronaviruse/who-china-joint-mission-on-covid-19-final-report.pdf) (Year: 2020).*

* cited by examiner

*Primary Examiner* — Mark V Stevens
(74) *Attorney, Agent, or Firm* — Witters & Associates; Steve Witters

(57) ABSTRACT

A method of reducing the virulence of microbes in or on the human body and a method of sanitizing or disinfecting a surface, area, object, or porous or non porous material is provided. The methods comprise applying or injecting a solution having an effective amount of a conjugated diene for substantially reducing the virulence of the microbes or sanitizing or disinfecting a surface, area, object, or porous or non porous material.

12 Claims, 4 Drawing Sheets

Figure 1:
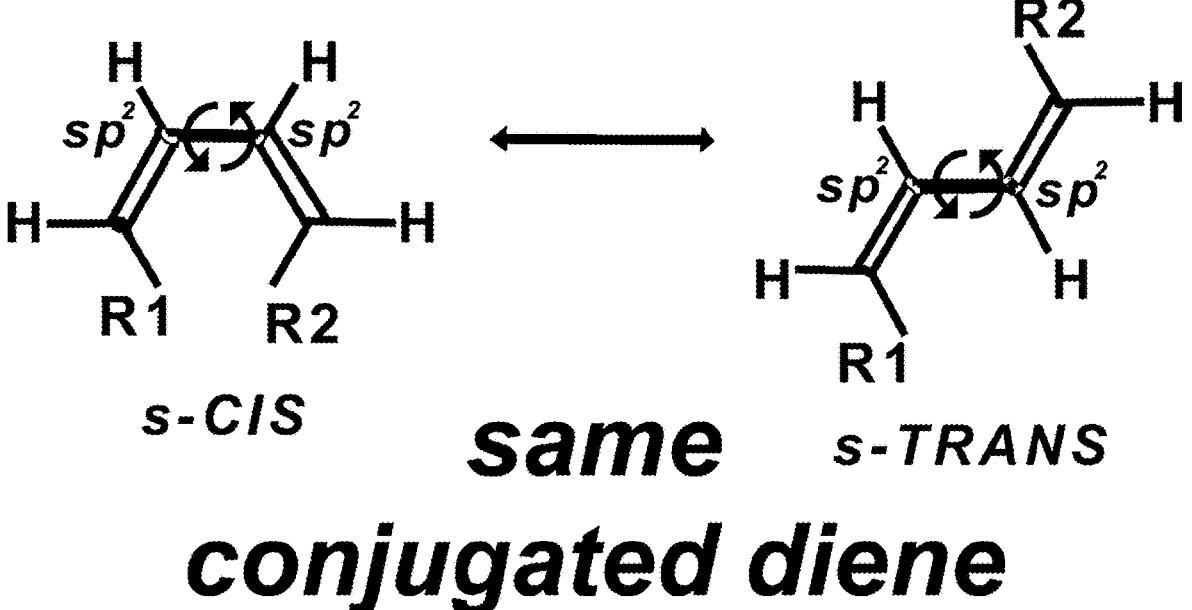

$\hat{y} = 2.45X + 2.57$ $p < 0.01 \; r = 0.9635$

DAYS DURATION COVID-19 SYMPTOMS

DAYS POST COVID-19 SYMPTOM ONSET TO BEGIN NEBULIZING LA(ISO)

SOLUTION AND METHOD FOR REDUCING THE VIRULENCE OF VIRUSES, BACTERIA, YEASTS, OR FUNGUS

CROSS REFERENCE TO RELATED APPLICATIONS

This application claims priority to U.S. application Ser. No. 16/938,753, filed Jul. 24, 2020 and PCT/US21/22447, filed Mar. 16, 2021, both of which claim priority to U.S. provisional application No. 63/003,249, filed Mar. 31, 2020, and U.S. provisional application No. 62/961,994, filed Jan. 16, 2020, the disclosures of which are hereby incorporated by reference in their entirety.

FIELD OF THE DISCLOSURE

The present disclosure relates to solutions and methods for reducing the virulence of microbes such as viruses, bacteria, yeasts, and fungus.

BACKGROUND

Microbes such as viruses, bacteria, yeasts, and fungus have been the cause sicknesses, hospitalizations, and deaths. They are also responsible for large costs in terms of health care, drugs, and for the indirect costs due to non-attendances at work and schools. A recent example of large costs incurred by society with such microbes is the SARS COV 2 (COVID-19) pandemic.

The spread of microbes may become epidemic in nature and may cause deaths, especially among vulnerable individuals such as the elderly and children and in immunosuppressed individuals.

The microbes may cause respiratory infections. In a survey conducted in the United States in 1995, infections of the upper respiratory ways were the main cause of medical examination before the General Practitioner's and Emergency clinics, with 37 million medical examinations and 52% of patients with uncomplicated upper respiratory infections, treated with antibiotics according to the "National Ambulatory Medical Care Survey".

The most widely used method of treatment of respiratory infections is the administration of antibiotics, and in many cases, antibiotics are administered without a real and actual need and may even have detrimental effects on the patient, It may be desired to provide solutions and methods for reducing the virulence of microbes.

SUMMARY

In one aspect of the present disclosure, a method of reducing the virulence of microbes in or on the human body is provided. The method comprises applying a solution to at least one of a mouth, nasal cavities, lungs, eyes, skin, and vagina, or injecting a solution intravenously, wherein the solution comprises an effective amount of a conjugated diene for substantially reducing the virulence of the microbes.

In another aspect of the present disclosure, a method of sanitizing or disinfecting a surface, area, object, or porous or non porous material is provided. The method comprises applying an effective amount of a conjugated diene to the surface, area, object, or porous or non porous material.

In an additional aspect of the present disclosure, a method of reducing the virulence of microbes in a human body comprises applying to the human a solution to at least one of a mouth, the nasal cavities, the lungs, the eyes, or the vagina, or injecting a solution intravenously. The applied or injected solution comprises a conjugated diene having a structure of R1-C=C—C=C—R2 in an amount effective for at least a log 2 kill of the microbes within two minutes of the applying or injecting of the solution.

In further aspect of the present disclosure, a method of sanitizing or disinfecting a surface, area, object, or porous or non porous material comprises applying an effective amount of a conjugated diene having a structure of R1-C=C—C=C—R2 to the surface, the area, the object, or the porous or non-porous material. A solution comprises the effective amount of the conjugated diene for at least a 2 log kill of microbes within two minutes of the applying of the solution.

BRIEF DESCRIPTIONS OF THE DRAWINGS

Figure 2:
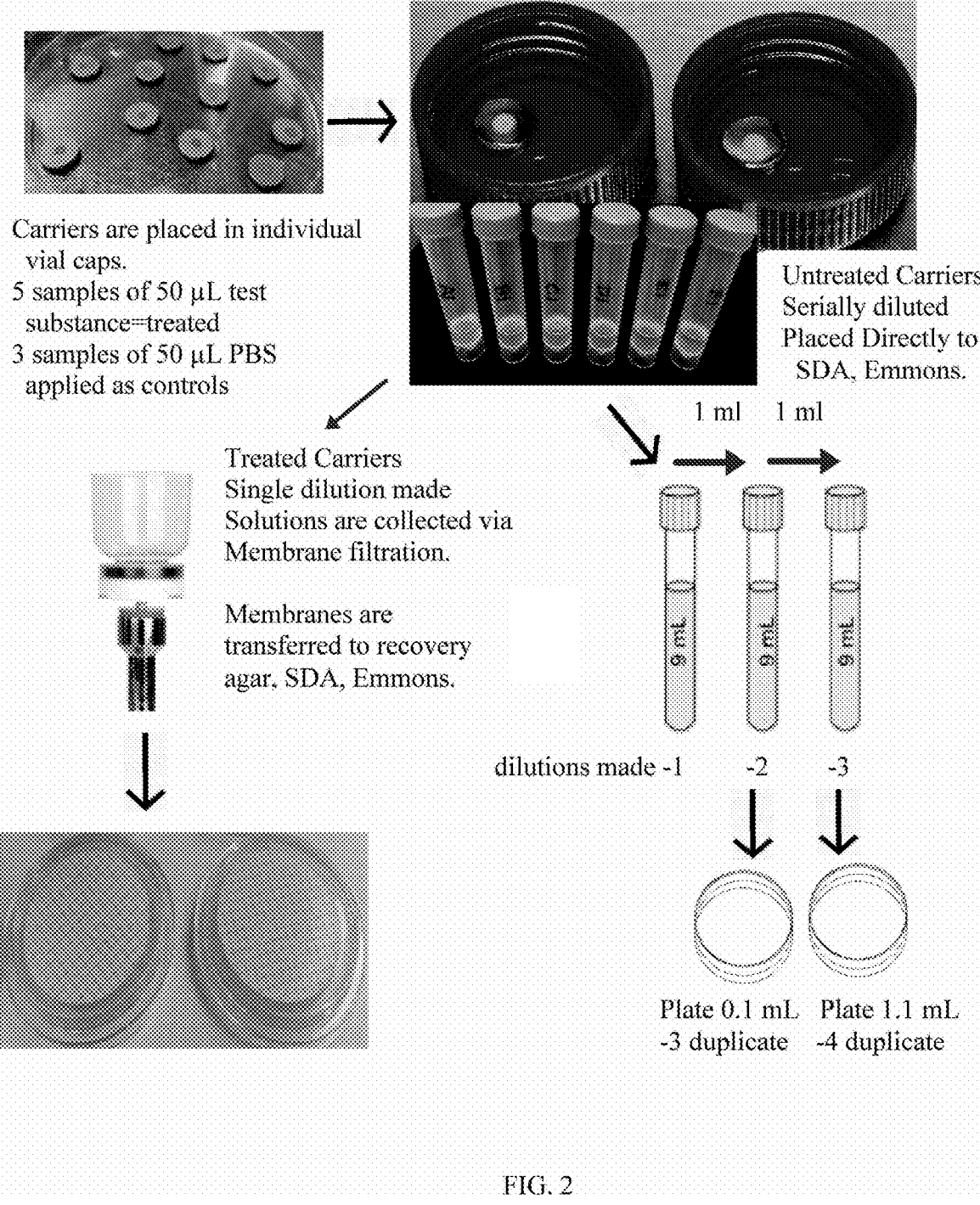
Figure 3:
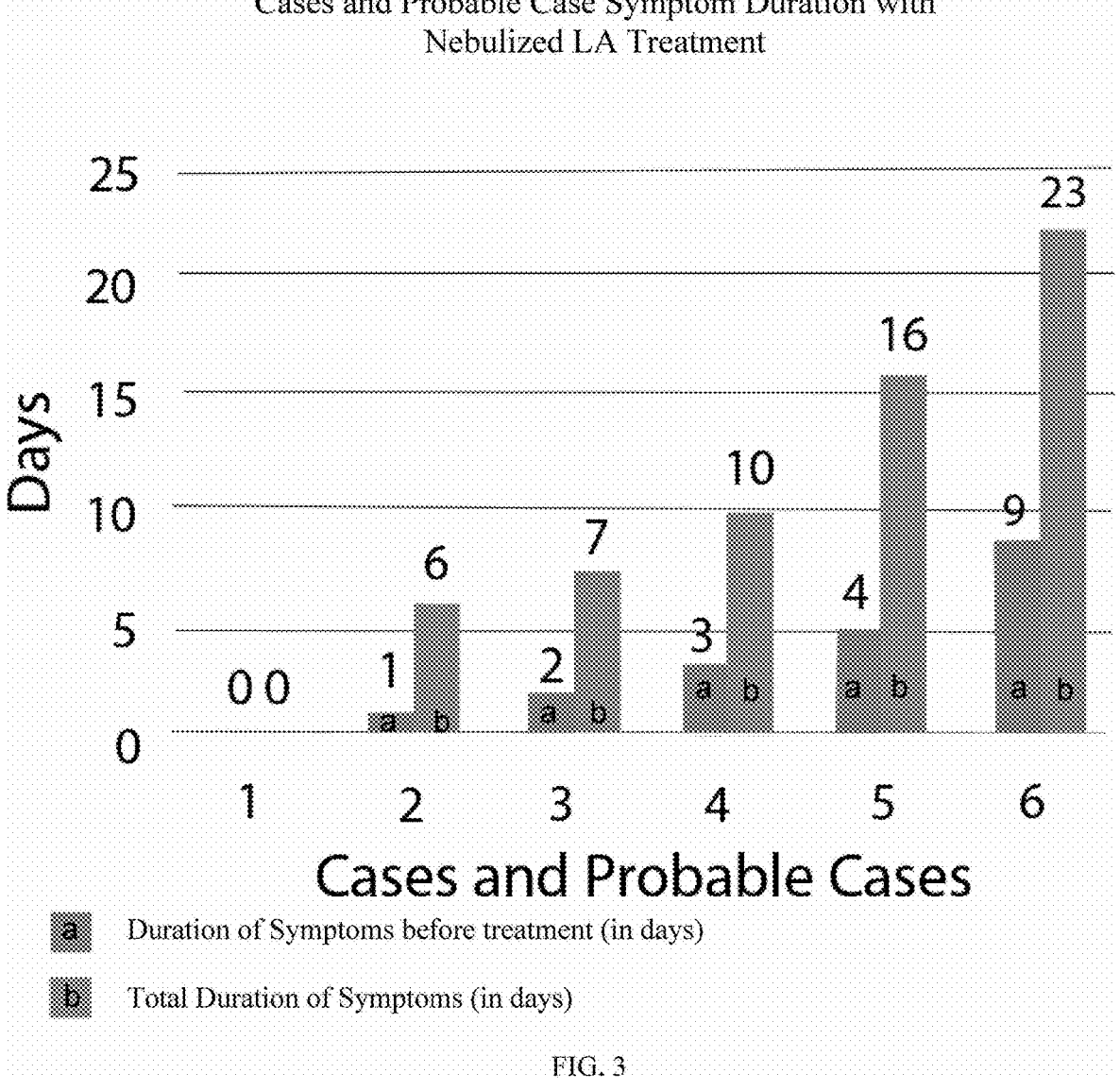
Figure 4:
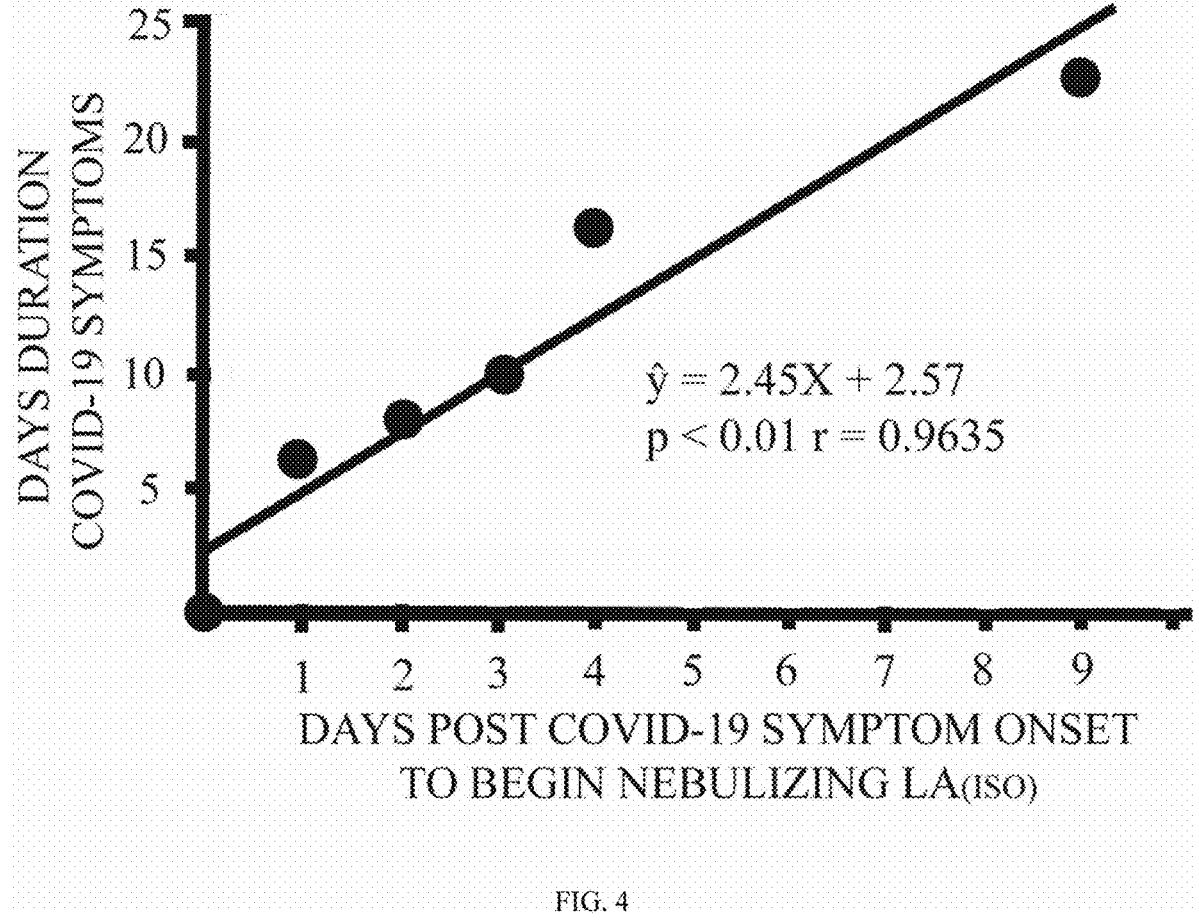

The foregoing and other features of this disclosure will become more fully apparent from the following description and appended claims, taken in conjunction with the accompanying drawings and examples. Understanding that these drawings depict only several embodiments in accordance with the disclosure and are, therefore, not to be considered limiting of its scope, the disclosure will be described with additional specificity and detail through use of the accompanying drawings, in which:

FIG. 1 shows an illustrative example of a conjugated diene that may be used in the presently disclosed solution and method for reducing the virulence of microbes;

FIG. 2 illustratively shows a test method of Example 1,

FIG. 3 shows the total symptom duration which is affected by the time nebulized LA treatment is started after symptom onset, and FIG. 4 shows a correlation between 'when beginning treatment' and 'length of reported COVID-19 related symptoms.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In at least one embodiment of the present disclosure, a method of reducing the virulence of microbes in or on the human body is presently disclosed. The method comprises applying a solution to at least one of a mouth, nasal cavities, lungs, eyes, skin, and vagina, or injecting a solution intravenously, wherein the solution comprises an effective amount of a conjugated diene for substantially reducing the virulence of the microbes. For example, the solution may be applied with a vaporizer, as nasal spray, or with a mister.

The effective amount of the conjugated diene may block cell penetration of microbes by adhering to hydrophobic structures made further electron poor by basic amino acids or other chemicals in the viral envelope. This may include the spike protein of SARS COV 2 (COVID-19) and other viruses and microbes that involve similar structures. For example, viruses such as Coronavirus, Cornidovirineae, and/or Coronaviridae.

The conjugated diene, for example conjugated linoleic acid, may poses two structure-activities for attaching to hydrophobic electron poor structures to alter cell function, cause apoptosis or sequester small molecules or portions of larger molecules. As used herein, the term conjugated diene includes, but is not limited to, conjugated linoleic acid and isomerized linoleic cationic salts (ILCS). The first structure activity may be a centrally located conjugated diene and the second structure activity may be two aliphatic arms of sufficient length with capacity to rotate about the $sp^2$-$sp^2$ bond, from trans to cis and to attach and hold structures by hydrogen bonds. For example, FIG. 1 may show an illustrative example of a conjugated diene that may be used in the presently disclosed solution and method for reducing the virulence of microbes.

The conjugated diene may have one arm with a carboxyl group or an acidic moiety or an electronegative element such as a cation and the other arm may have an aliphatic chain. The two arms may trap hydrophobic regions such as tryptophan or phenylalanine on microbial surfaces or molecules thru a combination of electrostatic, orbital, and steric forces.

For example, the conjugated diene of the present disclosure may have a structure of R1-C=C—C=C—R2, wherein R1 and R2 each have at least one carbon. In at least one embodiment, R1 may have an aliphatic chain and R2 may have a carbon chain and a carboxyl group or an acidic moiety.

Hydrophobic structures may anchor many microbes to mammalian cells and the conjugated diene may target these anchors to limit their virulence. Since the SAR CoV S1 spike protein has both tryptophan and phenylalanine within its anchoring portions and sequence homologies to SAR CoV 2, the conjugated diene may bind with these sites to limit viral anchoring. Such a process may block propagation of the viruses to adjacent or distant epithelia within an airway. This may in turn slow the progression of symptoms until the host develops sufficient immunity to prevent systemic progression.

The application of the solution having an effective amount of a conjugated diene in a pharmacologically acceptable vehicle may limit or reduce the virulence of the microbes. An effective amount of the conjugated diene in the pharmacologically acceptable vehicle may be at a concentration of the conjugated diene between 0.1 millimolar and 500 millimolar, between 0.2 millimolar and 60 millimolar, between 1 millimolar and 100 millimolar, between 1 millimolar and 10 millimolar, between 1 millimolar and 5 millimolar, or between 5 millimolar and 10 millimolar.

Conjugated diene may disorder the capacity of *P. aeruginosa* Quorum Sensing Agents to initiate slime formation at dilutions that permit *P aeruginosa* growth. This interference of Quorum Sensing Agents with the conjugated diene may occur in a range of concentration of the conjugated diene in the pharmacologically acceptable vehicle between about 1 millimolar and 10 millimolar. This inhibition of slime formation with the conjugated diene may provide for limiting the expression of virulence in the gut microbiota and other microbiomes.

In at least one embodiment, the conjugated diene has isomerized linoleic cationic salts (ILCS), a C18 conjugated diene aka "conjugated linoleic acid". ILCS is generally recognized as safe and exposure to humans may pose little or no risk beyond local discomfort. ILCS may have broad spectrum lethality to viruses, gram positive and gram negative bacteria, yeast and fungi. ILCS may have antimicrobial efficacy which may included antibiotic resistant bacteria such as methacillin resistant *Staphylococcus* and vancomycin resistant *Enterococcus* (Changaris, 2018; Changaris and Sullivan, 2019). For example, ILCS may have lethality to *Aspergillis brasiliensis*.

An ILCS cleanser may provide a cosmetically acceptable experience for bathing, washing hair, mucous membranes and barrier deficient skin (Changaris, 2020). While generating cosmetic formulations of a conjugated diene potassium salt, ILCS may form a hard gel. This gel may solidify over days to weeks. Cosmetically acceptable carriers may include non GMO plant oils, aminos, and vitamins. Higher concentrations of ILCS may form increasingly viscous gels with changes in color.

Certain amino acids may increase the viscosity of gels, while others reduce or even possibly increased the hydro-gel tension. Additionally, those amino acids may change the color of the gel. We have deduced that these changes may reflect conformational changes interacting with the conjugated structure deep within the ILCS, and in fact, these amino acids, when minimally modified, are similar to QSAs. This relaxation and color effect may be caused by structures similar to a Quorum Sensing Agents (QSAs), amino acids with correlative QSA of gram positive and negative bacteria as well as fungi and yeasts (Sprague, 2006) or plant communicating molecules (Ding and Ding, 2020). QSAs may provide for the interactions between ILCS and viruses, gram positive and gram negative bacteria, yeast and fungi, and the mechanism of inhibition and cidal activity. These amino acids are hydrophobic and rich in electron-poor moieties. ILCS possesses a hydrophobic aliphatic arm and a hydrophilic one with a single carboxyl group. The centrally located conjugated diene may serves to anchor electron poor hydrophobic structures and limit quorum sensing activities. This may have the effect of blocking communication between microbes, defined by quorum sensing.

It is known that the conjugated diene rotates around the single carbon bond between the two dienes (Ashenhurst, 2020). This rotation maintains a dynamic equilibrium between the s-cis and s-trans without breaking the molecular bond. Any given conjugated diene molecule may maintain a dynamic equilibrium between s-cis and s-trans as shown in FIG. 1. This unique shared sp2-sp2 pi orbitals, in connection with the long aliphatic arms, combined, may generate strong and rapid interactions with quorum sensing molecules and surface amino acids.

The sp2-sp2 pi bond may allow the s-trans to rotate into the s-cis position after attracting an electron poor hydrophobic portion of a molecule such as histidine, proline, tryptophan, phenylalanine, lactones, or hydrophobic moieties. With a multi-carbon chain on either side of the sp2-sp2 bond, the arms may rotate from s-trans towards s-cis positions. The arms may fit around amino acids, peptide-sized molecules, or "squeeze" cell surfaces which may hold amino acids and peptide-sized molecules. Many QSAs have hydrophobic electron poor components that can fit here. The transition back and forth between the s-cis and s-trans configurations may permit the molecule to trap molecules or regions of larger molecules. The cation salt of the carboxyl group may tend to "lock" a molecule with the "right" conformation in place. The presence of mixed isomers of C18 linoleic acid may enhance the range of molecules that might be trapped by this mechanism.

In at least one embodiment of the present disclosure, a method of reducing the virulence of microbes in or on the human body comprises applying a solution to at least one of a mouth, nasal cavities, lungs, eyes, skin, and vagina, or injecting a solution intravenously. The solution has an effective amount of a conjugated diene for substantially reducing the virulence of the microbes.

The conjugated diene may have a structure of R1-C=C—C=C—R2 as shown in FIG. 1. R1 has at least one carbon and R2 has at least one carbon. R1 may have an aliphatic chain and R2 may have a carbon chain and a carboxyl group or an acidic moiety. The conjugated diene may have up to 40 carbons. For example, the conjugated diene may have between 8 carbons and 30 carbons. The aliphatic chain in R1 may have between 3 carbons and 13 carbons. For example, the aliphatic chain in R1 may have between 6 carbons and 9 carbons. The carbon chain in R2 may have between 2 carbons and 15 carbons. For example, the carbon chain in R2 may have between 4 carbons and 5 carbons.

Corona viruses have received significant attention as they infect many animals causing significant animal husbandry issues. Over the last three decades three corona viruses have transcended the animal to human host to cause substantial deaths to the human population. The latest remains the SARS COV 2 (following MERS and SARS COV). A great deal of attention has been focused on the spike protein(S) of the corona viruses. SARS COV and SARS COV 2 appear to have preserved the hydrophobic amino-acid-anchoring tool, using tryptophan and likely phenylalanine buried in an S spike protein, also rich in basic amino acids. And this "docking" region has further been identified as the mono-carboxypeptidase Angiotensin Convering Enzyme-2. see Changaris, David G., James J. Miller, and Robert S. Levy. "Angiotensin II Generated by a Human Renal Carboxypeptidase." Biochemical and Biophysical Research Communications 138, no. 2 (July 1986): 573-79. https://doi.org/10.1016/S0006-291X(86)80535-6.

Isomerized linoleic cationic salts, conjugated diene, or conjugated linoleic acid may block viral fusion by selectively binding the S-spike-protein-anchor tryptophan and other hydrophobic amines. The spike protein of SARS COV 2 (COVID-19) and other viruses and microbes may use such structures as "docking" points to initiate cell entry. ILCS may have the capacity to block viral fusion by binding to these docking points.

The spike or S protein remains the main focus of neutralizing antibody study and vaccine design (Tortorici and Veesler, 2019). Detailed analysis the S1/S2 spike region allows review of surface amino acid sequencing and comparison through many corona species (Walls et al., 2020). Analysis of the S protein has led to mechanisms for antibody synthesis and drug interventions to disrupt some aspect of the viral intrusion process. The analysis of the Data S1. Amino Acid Sequence Alignment of Sarbecovirus S Glycoproteins (Walls et al., 2020) approximately 1273 amino acids shows this collection contains 40% hydrophobic amino acids and 9% basic amino acids. With nearly 50% of the S1/S2 amino acid composition defined this way it may be reasonable that some of these hydrophobic structures would be both hydrophobic and electron poor due to proximity to the basic regions. Some investigations have shown specifically that tryptophan performs function as an initial anchor with a quaternary structure that may be wrapped by ILCS, making this anchor unavailable. For example, Alpha-CoV has recognition of cell entry receptors in the form of tryptophan. Conjugated diene, ILCS, or conjugated linoleic acid may wrap the tryptophan anchor, making it inaccessible to the cell entry receptors.

Tryptophan and phenylalanine together make up 7% of the Data 1 set of SAR Cov-2 (Walls et al., 2020). They produce rapid changes in the viscosity of ILCS. This suggests ILCS may have an attraction for tryptophan or phenylalanine residues especially when adjacent to basic structures. Given the number of these amino acids some would likely be on the surface or superficial enough to become open as the ILCS moves toward it. SAR COV 2 may enter the cell through angiotensin converting enzyme 2 (ACE-2), a ubiquitous cathepsin mono-peptidase attached to the cell membrane. This enzyme would need to attract at least 4 carboxyl amino acids to cleave sequentially the first two amino acids in the angiotensin 1 sequence Asp-Arg-Val-Tyr-Ile-His-Pro-Phe-His-Leu|Val-Ile-amino acids. These amino acids may disorder the viscosity of ILCS.

Potassium hexadiene (pH 9) was shown to have little reduction in microbial growth as compared to ILCS efficacy of 8-10 log reduction, indicating that the aliphatic and carboxylic arms participate in microbial lethality. The long flexible arms of ILCS may create a non-destructive hydrophobic pocket around the conjugated diene, much like Diels-Alderase creates an active site pocket (Oikawa, 2016).

Low concentrations 3-10 mM of ILCS may be effective for inactivating virus populations. ILCS, conjugated linoleic acid, or conjugated diene is generally recognized as safe by the FDA. The aerosolizing of millimolar concentrations of conjugated diene may provide for delivery to nasal and oral cavities as well as trachea and lungs which may be effective in reducing the virulence of microbes. ILCS alone may have a salutary effect on mobilizing mucous when coupled with postural drainage during pulmonary therapy. The basic nature of the ILCS solution may drive the local pH towards 8, where rapid viral inactivation of some corona species has been reported in vitro (Sturman et al., 1990).

Corona viruses possess an array of peplomers with hydrophobic amino acids that suggests ILA (Isomerized Linoleic Acid), conjugated diene, conjugated linoleic acid, or ILCS may encase these and interfere with fusion to host cells. ILCS preparations at pH 7-10.5 remain soluble and effective at killing a wide range of microbes to pH 7.8-8.0 when diluted with artificial hard-water. The ILCS preparations have a pH of 9-10.5 and we know that some corona virus species are inactivated at or above pH 8 (Sturman et al., 1990).

A 2-50 mM ILCS spray or wash for the nasopharynx cavity has reduced symptoms associated with viral illnesses such as pharyngitis and rhinorrhea. With respect to pharyngitis, for a significant minority, a topical application of a low concentration of xylocaine helps severely sore throats with the first few gargles or spray applications. After these initial treatments xylocaine is rarely needed.

In at least one embodiment, the disclosed method of reducing the virulence of microbes in or on the human body comprising applying a solution to at least one of a mouth, nasal cavities, lungs, eyes, skin, and vagina, or injecting a solution intravenously, wherein the solution comprises an effective amount of a conjugated diene for substantially reducing the virulence of the microbes. The solution may further comprise at least one of water, amino acid, cations, and alcohol. For example, the solution may comprise the cations at least at a substantially molar equivalent to the conjugated diene in the solution.

The cations may have at least one of lithium, sodium, potassium, and rubidium. In at least one embodiment, the solution has sodium. In at least one other embodiment, the solution has potassium. The solution may comprise the cations at a molar ratio of the cations to the conjugated diene between about 1:1 and 5:1.

The solution may have a concentration of the conjugated diene between 0.1 millimolar and 500 millimolar, or between 0.2 millimolar and 60 millimolar.

In at least one embodiment, the disclosed method of reducing the virulence of microbes includes reducing the virulence of gram positive bacteria, gram negative bacteria, virus, fungus, yeast, or combinations thereof. The microbes may have a microbial surface containing at least one region having greater than 10% of histidine, proline, tryptophan, phenylalanine, lactones, or hydrophobic moieties. These lipid structures may provide a site for the binding of ILCS, and thereby reduce the virulence of the microbes. The presently disclosed method of reducing the virulence of microbes may provide for a substantial reduction of the virulence of the microbes in less than 60 seconds.

For example, the presently disclosed solution and method may provide for a rapid method and material for disinfecting or sanitizing solid surfaces, skin, or in the human body by reducing the virulence of *Candida albicans* and/or auris. In at least one embodiment, the solution has cosmetically acceptable plant soap. The disinfecting material may be applied a variety of ways such as spraying or any way known by persons having ordinary skill in the art for applying a liquid or flowable material. For example, disinfecting material may be sprayed onto a surface or in a room, used as a soap, or otherwise applied to an item or person for disinfecting such as misting or spraying.

The disinfecting material may comprise an amount of isomerized linoleate potassium salt sufficient to achieve a desired disinfecting result. The disinfecting material may comprise poly unsaturated fats with the general formula $R'-C=C-C=C-R^2$.

*Candida auris*, an emerging lethal, drug-resistant invasive yeast, threatens all humans with its ease of transmission to carrier state. Hospitals have few tools to combat its lethal invasiveness in immunocompromised patients (30-60%) or disinfect carriers or treatment environments. Currently, the United States Center for Disease Control recommends (US-CDC) recommends using disinfectants approved for Clostridia. The use of these agents requires critical personal protection and training to reduce potential harm to use or be in close proximity. The United States Environmental Protection Agency (US-EPA) has established criteria for *C. auris*-disinfectant efficacy: (EPA MLB SOP MB-3500). To date no specific disinfectant has achieved approved status using this protocol. We have known for many years that isomerized linoleate potassium salt (ILPS) has broad spectrum cidal properties against both non-resistant and drug resistant bacteria, as well as yeasts of *Candida albicans* and *Malassezia* sp. Due to this fierceness of *C. auris*, we first validated the EPA procedure by showing that a simple, cosmetically acceptable body wash made with GRAS ingredients has disinfectant efficacy (100% kill of $10^6$-$10^8$ yeast/ml) against *C. albicans* (ATCC 1023 1) at 2 minutes exposure (p<0.0005, Welch's t-test). We then obtained the requisite *C. auris* AR-0381 strain from the AR Isolate Bank (CDC). The simple proprietary blend of a potassium soap ILPS showed similar efficacy against this *C. auris*. A 2-minute immersion completely disinfected (100% kill; p<0.00057, Welch's t-test) 10 mm stainless steel round "carries" inoculated with 6-8 log *C. auris* or *C. albicans* yeast. Respective controls grew 6-8 log *C. auris* or *C. albicans*. The vehicle alone showed less than 1 log efficacy against both. We propose the ILPS binding to the cell walls of *C. auris* and *C. albicans* resides within the shared pi-bonding in the central conjugated complex. Furthermore, we propose that the potassium salted carboxyl group alters the central conjugation to become conformationally lethal to these pathogens. This capacity of Isomerized Linoleic Acid does not disorder the gut biome as evidenced by its continued mass consumption as a GRAS human and nutritional supplement as well as its presence in the rumen cross species. Finally, this simple cosmetically acceptable plant soap is well tolerated in ordinary cosmetic use by the authors.

Since investigators in 2009 reported drug resistance within *Candida auris*, others have found numerous strains with either single or multi-drug resistance. Most appear to have evolved independently throughout the world. Expert hospitalists dealing with infectious disease recently wrote that *Candida auris* is a next step in the evolution of multi drug resistant pathogens, extending from bacterial resistance to this new fungal multi-resistant pathogen.

Reports further showed these newly evolved yeasts have invasive capacity with mortality rates of 20-40% in immunocompromised hospitalized patients. The US-CDC Arisolate Bank has over 20 strains with either single or multiple drug resistance. Recently the first publication outlining the advent of *C. auris* in Russia identified that, of those infected who did not receive treatment, 42% died. *C. auris* can also resist standard hospital disinfection procedures as well as colonize hospital workers without causing symptoms. Traditional approaches to such threats focus on creating drugs targeted on killing by disrupting internal vital systems of the pathogen. The resulting and enduring collateral damages includes both developing drug resistance and the disruption of the microbiome to allow new pathogens to colonize. Now, we have efforts to preserve the integrity of the microbiome while reducing the impact of a given pathogen. For example, the CDC's call for therapeutic agents to treat antibiotic resistant hospital associated infections (AR-HAT) now asks for, "Novel therapeutics and preventatives based upon preservation or the restoration of the human microbiome"

By inference, it appears that the use of targeted chemicals to invade and disorder the internal machinery of microbial growth has resulted in disruption of the human microbiome. Even a single dose of antibiotics shifts the populations to microbes less able to keep *Staphylococcus aureus* from colonizing. As remarkable as it were serendipitous, the discovery that GRAS isomerized linoleate potassium soaps effectively reduces growing populations of pathogens may serve this type of therapeutic preventative sought by the US-CDC.

The presence of internal conjugation within free fatty acids from plants changes the oils dramatically. The first physical change is the miscibility with water. Such fatty acids will form emulsions with water, ignoring the conventional wisdom, "oil and water do not mix." The four shared pi bonds provide a stable isomeric state. This appears to allow for stacking and cell wall adherence. This also allows for stable skincare products without the need for surfactants. The general cosmetic use of the potassium soaps of isomerized linoleate led to the clinical observation that washing with ILPS caused the clinical remission of acne. More detailed studies by a third party identified that it also suppresses the growth of methacillin resistant *Staphylococcus aureus*, vancomycin resistant *enterococcus, pseudomonas, aspergillus, Candida albicans, Helicobacter pylori*. These capacities extend to alkene conjugation found in punicic acid. Continued testing further identified efficacy to reduce the in vitro growth of *Malassezia* species and with appropriate adjuvants to clear associated infections of human skin. The decision to explore efficacy against *Can-*

*dida auris* followed the identification of in vitro efficacy and clinical effects personally witnessed but unreported on clinical candidal infections.

In at least one embodiment of the present disclosure, *C. albicans* and *C. auris* are disinfected on a solid surface with a 2-10 minute exposure to a 1-20%, 2.5-12% or, 6-12% isomerized linoleate potassium salt. For example, antimicrobial treatments involving poly unsaturated fats with the general formula $R'—C=C—C=C—R^2$, wherein R' is an aliphatic, with or without unsaturated bonds, and $R^2$ contains an aliphatic chain, with or without unsaturated bonds, and carboxyl group coupled with a metal halide such as sodium or potassium.

In at least one embodiment of the present disclosure, a method of sanitizing or disinfecting a surface, area, object, or porous or non porous material is provided, The method comprises applying an effective amount of a conjugated diene to the surface, area, object, or porous or non porous material. For example, an effective amount of conjugated diene may be sprayed, wiped, or otherwise applied onto the surface, area, object, or porous or non porous material that is being treated.

EXAMPLES

Example 1

Long-standing regulatory perspectives hold that all plant-oil soap salts lack direct antimicrobial capacity. We demonstrate that the potassium salt of isomerized linoleic acid [UNII: 70S2158RCI], a plant-oil soap and conjugated diene, at 0.42 M exceeds the required 5 log kill rate for the invasive antifungal-resistant *Candida auris* (AR-0381) within 1 min by in vitro testing to fulfill the US EPA standards for *C. auris* disinfection. Testing this plant salt against *Candida albicans* (ATCC 10231) also demonstrated greater than 5 log kill rates at 1 min. Current regulatory guidance from the Environmental Protection Agency (EPA) states: "In 1988, the EPA determined that soap salts have 'no independent pesticidal activity' in antimicrobial products, and must be classified as inert ingredients in those products (see 40 CFR 153.139). Antimicrobials that still contain soap salts as active ingredients are considered misbranded (US Environmental Protection Agency. 1992).

Since this determination in 1992, studies published within the US patent literature have indicated that isomerized linoleic plant salts have broad-spectrum lethality toward gram-positive and gram-negative bacteria, yeast, and fungi (Changaris. 2018: Changaris and Sullivan. 2019). The reported antimicrobial efficacy included antibiotic-resistant bacteria, such as methicillinresistant *staphylococcus* and vancomycin-resistant enrero coccus, as well as *Candida albicans* (Changaris. 2018). It appeared to us that the mechanism of action may be outside of the known mechanisms classically used by microbes to develop resistance (Reygaert. 2018).

Consequently, we tested potassium-isomerized linoleic acid against the invasive antifungal-resistant *Candida auris* (AR-0381). The CDC identifies *C. auris* as a major threat to the world because immunocompromised individuals suffer fatality rates ranging from 10% to 60% (Lockhart et al. 2017). The resistance pattern of the isolate (AR Isolate Bank #0381), shown in Table 1, supports their perspective. The genome sequence is available in the AR Isolate Bank as Biosample Accession #5AMN05379608 (CDC, 2016).

TABLE 1

| Antimicrobial Sensitivities for *Candida auris*, (AR-0381) | |
| --- | --- |
| Drug | MIC (µg/mL) |
| Amphotericin 81 | 0.38 |
| Anidulaftrngin | 0.25 |
| Caspofungin | 0.13 |
| Fluconazolc | 4.00 |
| Flucytosine | 2.00 |
| Iuaconazole | 0.13 |
| Micafungin | 0.13 |
| Posaconazolc | 0.06 |
| Voriconazole | 0.03 |

We used EPA protocol MB-35-00 for testing disinfectants against *C. auris* (US Environmental Protection Agency. 2017, 2020) and *C. albicans* ATCC 10231, a yeast common in package spoilage of food and cosmetics.

Potassium hexadiene contains the central four-carbon conjugated diene structure absent the carbon arms of potassium-isomerized linoleic acid. To identify whether the conjugated carbons by themselves are sufficient, we tested this compound using the same protocols.

Materials and Methods

ILCS Production

We prepared potassium-isomerized linoleic acid using potassium hydroxide purchased from Spectrum Chemical (New Brunswick Ni USA) and isomerized linoleic acid from Quanao Biotech Co., Ltd. (Shaanxi. China) and Stepan Co. (Northfield. IL, USA). We also prepared and tested the salt using in-house isomerized linoleic acid prepared from safflower purchased from Jedwards (Stockton. MA. USA). The final solution contained 0.42 M potassium-isomerized linoleate, 15 mM aspartic acid, and 2.2 M ethanol. We tested 5 batches produced with difference sources of isomerized linoleic acid (Test Substances 1-5).

Antimicrobials against *C. auris*: MB-35-00 (US Environmental Protection Agency, 2017, 35-40)

The EPA test protocol for testing hard surface disinfection of *C. auris* (AR0381) with antifungal resistance includes an overnight culture of *C. auris* (AR.0381) shaken at 200 rpm at 30° C. From this culture, 8 mL was harvested by centrifugation, re-suspended in 2-3 mL phosphate-buffered saline (PBS), and mixed with a 3-part soil load including bovine serum albumin (BSA), yeast extract, and mucin. Metal carriers (10 mm) were inoculated (10 µL culture+soil load) and dried in a desiccator under vacuum (~70 min). The disk surface was coated with the test substance at 0.42 M (50 µL) for up to 10 min. Following incubation, the carriers were transferred to 10 mL neutralization solution (Sabouraud Dextrose Broth [SDB], a common yeast-mold growth media) for subsequent harvesting on membrane filters. The filtered membranes were transferred to Sabouraud Dextrose Emmons Agar (SDEA) plates to culture for 120 hours at 31° C. Controls consisted of PBS (50 µL) applied to inoculated metal disk carriers, subsequently transferred to 10 mL neutralization solution (SDB), diluted serially in PBS, and plated directly to SDEA plates, See FIG. 2.

Strains and Materials

*C. auris* (AR-0381): The CDC Isolate Bank (Atlanta, GA, USA) graciously provided *C. auris* (AR-0381). This isolate has antimicrobial resistance to amphotericin B1, anidulaflingin, caspofungin, fluconazole, fiucytosine, itraconazole, micafungin, posaconazole, and voriconazole. The entire genomic sequence is available, and multiple resistance mechanisms are represented with this single isolate (CDC, 2016).

*Candida albicans* (ATCC 10231): We purchased *C. albicans* (ATCC 10231) from ATCC (Gaithersburg, MD, USA).

Test Carriers: We purchased flat metal carriers from Pegen Industries (part number #430-107L). We prepared and qualified these per EPA protocol (US Environmental Protection Agency, 2017).

Soil Stocks: We prepared soil stocks with yeast extract powder (Ref RM027) purchased from Himedia, BSA (A2153) purchased from Sigma Life Science, and gastric mucin (cat #HY-B2196/CS-7626) purchased from Mod Chem Express per SOP MB-35-00 (US Environmental Protection Agency, 2017).

Cell Harvesting: We removed cells from the growth culture media using a Micro-Centrifuge obtained from Changzhou Jintan Sanhe Instrument Co., LTD. (Model TGI6-W) at 10,000×g for 10 min in screw-top-cap vials purchased from Heathrow Scientific (Item HS 100600). The optical density of the inoculate was defined at 15-19 OD600 in PBS with the Ultrospec 10 Cell Density Meter from BioChrom (Holliston, MA, USA) prior to dilution in the soil load. Samples were diluted 1:10 in PBS to obtain absorbance readings between 1.5 and 1.9.

Membrane Filtration: Treated yeasts were collected using a combination of the Rocker (Cat #200300-01) and 47 mm PES membranes with a 0.45 micron pore size obtained from Sterlitech (Catalog #PE54547100). Magnets were used to hold the carriers in place during pouring.

SDEA, recovery agar: We purchased dextrose anhydrous (Item NCMO 121 6A), casein peptide type I (Item NCMO I 20A), and meat peptone no 3 (NCM0246A) from Neogen Culture Media (Lansing, MI, USA). We purchased agar from Himedia (RM201) (L.B.S. Marg, Mumbai, India).

Sabouraud Dextrose Agar, Emmons Modification Per Liter:
Dextrose 20.0 g
Casein Peptone 5.0 g
Meat Peptone 5.0 g
Agar 15.0 g Common Reagents
PBS: We generated stock solutions of PBS lox and PBS Ix using sodium chloride (1528090) from Innovating Science (Avon, NY. USA), potassium chloride from Bearclaw Sales (Cooke City, MI, USA), and sodium phosphate dibasic, anhydrous (89-1442) and potassium phosphate monobasic (884250) from Carolina Biological Supply Company (Burlington. NC. USA).

Growth media/agars: We purchased SDB (Himedia Ref GM033) from Weber Scientific (Hamilton. NJ, USA) and CHROMagar *Candida* (Ref CA222) from local distributors.

Water for Injection: <USP1231>: Purified water that satisfies the USP Standards for endotoxin <USP85>, bulk water <USP645>, and total organic carbon <U5P643> were produced in house.

Results

Potassium-isomerized linoleic acid showed greater than 5 log kill rates for both *C. albicans* and *C. auris* for all carriers with two separately manufactured lots at 1 min. This satisfies the US EPA standards for *C. auris* disinfection (EPA. 2020). A 10-min test, the longest time allowed per the SOP, showed greater than 5 log kill rates. In fact, the kill rates ranged between 5 and 7 logs in all testing runs (Tables 2 and 3). Potassium sorbate kill rates on both organisms were limited to less than one log.

TABLE 2

| | | | *Candida albicans* | | | |
|---|---|---|---|---|---|---|
| Assay | Salt Batch | Exposure (min) | Control Disks | Density (log) | Test Disks | Density (log) |
| 1 | 1 | 10 min. | n = 2 | 6.2, 6.6 | n = 2 | All No Growth |
| 2 | 2 | 2 min. | n = 3 | 6.2, 6.1, 6.3 | n = 3 | All No Growth |
| | 3 | 2 min. | | | n = 7 | All No Growth |
| 3 | 4 | 2 min. | n = 3 | 6.6, 6.5, 6.6 | n = 7 | All No Growth |
| 4 | 4 | 1 min. | n = 3 | 5.2, 5.4, 5.4 | n = 5 | All No Growth |
| | 5 | 1 min. | | | n = 5 | All No Growth |
| Potassium Sorbate | | 1 min. | | | n = 2 | 4.8, 4.9 |

TABLE 3

| | | | *Candida auris* | | | |
|---|---|---|---|---|---|---|
| Assay | Salt Batch | Exposure (min) | Control Disks | Density (log) | Test Disks | Density (log) |
| 5 | 1 | 10 min. | n = 3 | 5.0, 5.0, 5.5 | n = 9 | All No Growth |
| 6 | 1 | 10 min. | n = 3 | 5.7, 5.7, 5.5 | n = 7 | All No Growth |
| 7 | 1 | 10 min. | n = 3 | 6.1, 5.9, 5.9 | n = 7 | All No Growth |
| | 2 | 10 min. | | 6.6, 6.5, 6.6 | n = 7 | All No Growth |
| 8 | 1 | 2 min. | n = 3 | 5.7, 5.8, 5.9 | n = 5 | All No Growth |
| | 2 | 2 min. | | | n = 5 | All No Growth |
| 9 | 4 | 2 min. | | 5.7, 5.7, 5.7 | n = 5 | All No Growth |
| | 5 | 2 min. | | | n = 5 | All No Growth |
| Potassium Sorbate | | 2 min. | | | n = 3 | 5.0, 4.9, 4.9 |
| 10 | 1 | 1 min. | n = 3 | 5.7, 5.9, 5.9 | n = 5 | All No Growth |
| | 2 | 1 min. | | | n = 5 | All No Growth |
| | 4 | 1 min. | | | n = 5 | All No Growth |
| | 5 | 1 min. | | | n = 5 | All No Growth |

Kill rates for potassium-isomerized linoleic acid prepared in house were similar to those made from starting materials from Quanao Biotech Co., Ltd., China or Stepan. USA.

Discussion

We limited these studies to surface disinfection of inanimate objects. However, cosmetically acceptable preparations of potassium-isomerized linoleic acid are used in the open market. Cosmetic uses include use on the hair, face, skin, and in the mouth, nasal cavity, and vagina (Changaris. 2020). Potassium-Isomerized Linoleic Acid Satisfies EPA Protocol for Disinfection of *Candida auris* (AR-0381) and *Candida albicans*.

We hypothesize that the conjugated diene of potassium-isomerized linoleic acid may be targeting dienophilic structures on the surfaces of microbes. If a dienophile on a microbial surface were to substantially drain the shared sp2-sp2 electrons, the two arms might rotate and "scissor" together, placing the aliphatic and carboxyl arms in contact with the microbial surface. The lethality of potassium-isomerized linoleic acid suggests that these dienophilic structures of microbial surfaces play a role in essential surface mechanisms. The targeted binding of surface dienophilic structures does not fall within known microbial patterns for development of resistance (Reygaert. 2018). Potassium-isomerized linoleic acid possesses the capacity for use against a growing number of antibiotic-resistant species, and it has been demonstrated as effective against organisms with at least 3 mechanisms of resistance (Changaris, 2018: Changaris and Sullivan. 2019). An effective disinfectant devoid of the need for hazmat precautions may be provided. The capacity of potassium-isomerized linoleic acid to effect microbial growth reduction may involve yet undiscovered or undisclosed mechanisms.

Example 2

The following Example was performed by Utah State University, Institute for Antiviral Research, Logan, UT.
Procedure
Virus, Media, and Cell
SARS-COV-2 virus stocks were prepared by growing virus in Vero 76 cells. Test media used was MEM supplemented with 2% FBS and 50 µg/mL gentamycin.
Virucidal Assay
A 12% ICLS was received from the sponsor in liquid form. Sample was serially diluted 2-fold in water for final test concentrations of 90%, 45%, 22.5%, and 11.3%. SARS-COV-2 virus stock was added to triplicate tubes and media only was added to one tube of each prepared concentration to serve as toxicity controls. Ethanol was tested in parallel as a positive control and water only to serve as the virus control.
Compound and virus were incubated at room temperature for a contact time of 2 minutes. Following the contact period, the solutions were neutralized by a 1/10 dilution in test media containing 10% FBS.
Virus Quantification
Neutralized samples were combined for quantification for the average of triplicate tests. Samples were serially diluted using eight half-log dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus. All plates were incubated at 37±2° C., 5% CO2. On day 6 post-infection plates were scored for presence or absence of viral cytopathic effect (CPE). The Reed-Muench method was used to determine end-point titers (50% cell culture infectious dose, CCID50) of the samples, and the log reduction value (LRV) of the compound compared to the negative (water) control was calculated.
Controls
Virus controls were tested in water and the reduction of virus in test wells compared to virus controls was calculated as the log reduction value (LRV). Toxicity controls were tested with media not containing virus to see if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.
Results
Virus titers and LRV of 12% ICLS against SARS-COV-2 are shown in Table 4. Full toxicity was observed in the 1/10 and 1/100 dilutions for the 22.5%-90% samples, and in the 1/10 dilution of 11.3%. Because of this toxicity, presence of virus could not be ruled out in those wells; therefore the limit of detection for the 22.5%-90% tests was 2.7 and for the 11.3% was 1.7 log CCID50 of virus per 0.1 mL.
Virucidal activity was exhibited when 11.3% of the 12% ICLS was incubated with virus for 2 minutes, reducing virus from 3.5 log CCID50 per 0.1 mL in virus controls to below the limit of detection of 1.7 logs (>98%). Higher concentration from 22.5%-90% also reduced virus below the limit of detection of 2.7 log CCID50 per 0.1 mL (>80%). Further testing may be warranted to evaluate activity at lower concentrations and assess reproducibility.
Neutralization controls demonstrated that residual sample did not inhibit virus growth and detection in the endpoint titer assays in wells that did not have cytotoxicity. Positive controls performed as expected, though ethanol was also toxic to cells in the 1/10 dilution, limiting the detection of virus to <1.7 log CCID50 per 0.1 mL.

TABLE 4

|  | Concentration | Contact Time | Virus Titer[a] | LRV[b] |
|---|---|---|---|---|
| 12% ICLS | 90% | 2 minutes | <2.7 | >0.8 |
| 12% ICLS | 45% | 2 minutes | <2.7 | >0.8 |
| 12% ICLS | 22.5% | 2 minutes | <2.7 | >0.8 |
| 12% ICLS | 11.3% | 2 minutes | <1.7 | >1.8 |
| Ethanol | 63% | 2 minutes | <1.7 | >1.8 |
| Virus Control | n/a | 2 minutes | 3.5 | — |

[a]Log10 CCID50 of virus per 0.1 mL
[b]LRV (log reduction value) is the reduction of virus compared to the virus control Table 4 shows the virucidal efficacy of 12% ICLS against SARS-COV-2 after incubation with virus for 2 minutes at 22±2° C.

Example 3

The following Example was performed by Utah State University, Institute for Antiviral Research, Logan, UT.
Procedure
Virus, Media, and Cells
SARS-COV-2 virus stocks were prepared by growing virus in Vero 76 cells. Test media used was MEM supplemented with 2% FBS and 50 µg/mL gentamicin.
Virucidal Assay
A 12% ICLS was received from the sponsor in liquid form. Sample was serially diluted 2-fold in water for final test concentrations of 90%, 45%, 22.5%, and 11.3%. SARS-COV-2 virus stock was added to triplicate tubes and media only was added to one tube of each prepared concentration to serve as toxicity controls. Ethanol was tested in parallel as a positive control and water only to serve as the virus control.
Compound and virus were incubated at room temperature for a contact time of 2 minutes. Following the contact period, the solutions were neutralized by a 1/10 dilution in test media containing 10% FBS.

The experiment was repeated in the same way as described above testing lower concentrations of 11.3%, 1%, 0.5%, and 0.25%.

Virus Quantification

Neutralized samples were combined for quantification for the average of triplicate tests. Samples were serially diluted using eight half-log dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus. All plates were incubated at 37±2° C., 5% CO2. On day 6 post-infection plates were scored for presence or absence of viral cytopathic effect (CPE). The Reed-Muench method was used to determine end-point titers (50% cell culture infectious dose, CCID50) of the samples, and the log reduction value (LRV) of the compound compared to the negative (water) control was calculated.

Controls

Virus controls were tested in water and the reduction of virus in test wells compared to virus controls was calculated as the log reduction value (LRV). Toxicity controls were tested with media not containing virus to see if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.

Results

Virus titers and LRV of the 12% ICLS against SARS-COV-2 are shown in Table 5. Full toxicity was observed in the 1/10 and 1/100 dilutions for the 22.5%-90% samples, and in the 1/10 dilution of 11.3%. Because of this toxicity, presence of virus could not be ruled out in those wells therefore the limit of detection for the 22.5%-90% tests was 2.7 and for the 11.3% was 1.7 log CCID50 of virus per 0.1 mL. Virucidal activity was exhibited when 11.3% 12% ICLS was incubated with virus for 2 minutes, reducing virus from 3.5 log CCID50 per 0.1 mL in virus controls to below the limit of detection of 1.7 logs (>98%). Higher concentration from 22.5%-90% also reduced virus below the limit of detection of 2.7 log CCID50 per 0.1 mL (>80%).

In the second experiment testing 12% ICLS at lower concentrations, the 11.3% sample again reduced virus from 3.7 log CCID50 per 0.1 mL below the limit of detection (<1.7 logs, >99%) and the 1% sample reduced virus titer to 1.7 log CCID50 per 0.1 mL (99%). The 0.5% and 0.25% samples did not reduce virus by >1 log.

Neutralization controls demonstrated that residual sample did not inhibit virus growth and detection in the endpoint titer assays in wells that did not have cytotoxicity. Positive controls performed as expected, though ethanol was also toxic to cells in the 1/10 dilution, limiting the detection of virus to <1.7 log CCID50 per 0.1 mL

TABLE 5

|  | Concentration | Contact Time | Virus Titer[a] | LRV[b] |
|---|---|---|---|---|
| 12% ICLS | 11.3% | 2 minutes | <1.7 | >2.0 |
| 12% ICLS | 1% | 2 minutes | 1.7 | 2.0 |

TABLE 5-continued

|  | Concentration | Contact Time | Virus Titer[a] | LRV[b] |
|---|---|---|---|---|
| 12% ICLS | 0.5% | 2 minutes | 3.5 | 0.2 |
| 12% ICLS | 0.25% | 2 minutes | 3.3 | 0.4 |
| Ethanol | 63% | 2 minutes | <1.7 | >2.0 |
| Virus Control | n/a | 2 minutes | 3.7 | — |

[a]$Log_{10}$ CCID50 of virus per 0.1 mL
[b]LRV (log reduction value) is the reduction of virus compared to the virus control Table 5 shows replicate 1, virucidal efficacy of 12% ICLS against SARS-COV-2 after incubation with virus for 2 minutes at 22±2° C.

Example 4

ILCS Viscosity Changes Caused by 6% Amino Acids and Quorum Sensing Agent Phenylethanol ILCS 250 mM in water forms a hard non-Newtonian non-flowing gelatin. A simple viscometer, Digital Viscosity Meter (NDJ-8S, Shaoxing Worner Lab Equipment Co., Ltd., China) was used, recognizing the limitations of measuring a solid gelatin hydro-gel. The addition of 6% various amines changes viscosity, dramatically with tryptophan and phenylalanine. The ILCS was initially incubated at 120° F. overnight, equilibrated at 108120° F. prior to viscometry.

ILCS was made from potassium hydroxide (Spectrum Chemical, Louisville, KY), isomerized linoleic acid (Stepan, New Jersey), and USP WFI water (Ceela Naturals), to a final concentration 8% or 333 mM Potassium Linoleate (isomerized).

Many of the amino acids tested were purchased from Ajinomoto (NJ, USA), while tryptophan, proline, and phenylalanine were obtained from Purebulk (Oregon, USA). The Quorum Sensing Agent phenylethanol was purchased from Sigma Aldrich (GA, USA).

ILCS Viscosity Changes Caused by 6% Amino Acids and Quorum Sensing Agent Phenylethanol The gel and compound were incubated at 140° F. for 1-3 days followed by incubation 108° F. for 2-4 days. Tryptophan, phenylalanine, and phenylethanol all showed a two log-reduction in viscosity approaching liquefaction. This suggests a complex interaction with the conjugated diene consistent with our premise that hydrophobic structures are the initial target of the ILCS in its antimicrobial disinfection capacity.

Table 6 shows the viscosity change of 6% amino acid added to 8% ILCS (potassium). Viscosity measures with addition of various amino acids and bio-active agents 5 (milliPoise). These show phenylalanine, tryptophan, and phenylethanol all have intense interactions with the ILCS hydro-gel consistent with the trapping sequestration of these molecules by like-dissolves-like interactions.

TABLE

| | |
|---|---|
| Cysteine-HCl | 28400 |
| D Panthenol | 31600 |
| Alanine | 40700 |
| Niacinamide | 33800 |
| Arginine | 25600 |
| Methionine | 32350 |
| Valine | 31850 |
| Phenylalanine | 130 |
| Tryptophan | 21 |
| Iso-Leucine | 29900 |
| D L Panthenol | 28650 |
| Lysine-hcl | 30700 |

TABLE-continued

| | |
|---|---|
| Histidine base | 28050 |
| Aspartic acid | 25100 |
| Serine | 22300 |
| Threonine | 30650 |
| Phenyl ethanol | 110 |
| Lysine base | 26900 |

Example 5

Candida albicans ATCC 10231 were purchased from American Type Culture Collection (ATCC) (Manassas, VA). We received a gift of Candida auris AR-0381 kindly provided by the AR isolate Bank (CDC AR Isolate Bank, Atlanta GA). Isomerized linoleic acid (80% Free Fatty Acid) was purchased from Van Quanao Biotech Co., Ltd.

We prepared the Isomerized Potassium Linoleic Soap (IPLS) by mixing 0.384 kg potassium hydroxide (Spectrum Chemical Manufacturing Corp. Gardena, CA), 0.0957 kg Aspartic Acid (PureBulk Roseburg, OR), 0.6 kg 80% Isomerized Linoleic Acid (Xi'an Quanao Biotech Co., China), and 0.5 kg ethanol (PureBulk Roseburg, OR), in 3.402 kg Purified Sterile Water (USP <123 1>, <85>, <643> and <645>. The vehicle control consisted of the same proportions of this mixture absent the Isomerized Linoleic acid.

We followed the US-EPA standards for disinfecting C. auris, EPA MLB SOP NM-37-00 and EPA MLB SOP MB-35-00. This somewhat lengthy protocol was summarized within these methods in Section C:

"C. In brief, the OECD quantitative test method uses disks (1 cm in diameter) of brushed stainless steel as the carrier to represent a hard, non-porous surface. Each disk receives 10 µL of the test organism with a soil load incorporated into the inoculum. The inoculum is dried and exposed to 50 µL of the test substance; control carriers receive an equivalent volume of an innocuous control fluid. The contact time is allowed to elapse and a neutralizer is added at the end of the contact time. The neutralized carriers are vortexed and the resulting suspension is filtered to determine the presence of viable organisms. Based on mean $\log_{10}$ density values, the Log Reduction (LR) in the viability of the test organism on treated carriers is calculated in relation to the viability count on the control carriers. The LR value is used as the measure of product performance (i.e., product efficacy)."

The procedure was validated using Candida albicans ATCC 10231 (American Type Culture Collection; Manassas, VA). Candida auris AR-0381 was kindly provided by the AR Isolate Bank (CDC AR Isolate Bank, Atlanta GA).

Results

Initially, we dried Candida albicans (ATCC 10231) 50 microliters for a final 5.9-7.2 $\log_{10}$ CFU onto 9.52 mm metal carries prepared with a soil load (mucin, BSA, and yeast extract per EPA MLB SOP MB-35-00). We placed the individual carries into undiluted ILPS, or with phosphate buffered saline pH 7.4 as a control, for 10 minutes contact time. We transferred the carries to the specified recovery medium (SDB per EPA MLB SOP MB-35-00), and vortexed. We filtered the supernate thru a 0.44 micron filter. We cultured this filter in toto for survival counts. We processed the control carries similarly to determine survival counts. We recovered no Candida albicans colonies from the ILPS treated surfaces. The PBS treated controls cultured where 5.9 to 7.2 $\log_{10}$ CFU. We repeated this process over 5 independent experimental trials with similar results.

Dilution and Time Course for C. albicans: Repeat of the above procedure with ILPS diluted in "hard water" 1:3.5 prepared per EPA MLB SOP MB-35-00 showed 0.002% recovery rates with C. albicans. We exposed single carries prepared with C. albicans and soil load to ILPS for 8, 7, 6, 5, 4, 3, 2 and 1 minutes. Only the 1-minute-exposed carries showed growth of 158 CFU. Three control carries exposed to PBS for 8 minutes showed $7\times10^6$, $7.8\times10^6$, and $6.6\times10^6$ CFU.

Candida auris AR-0381 prepared per EPA MLB SOP MB-35-00: We dried 50 microliters containing 7.1-7.2 logs CFU C. auris onto 10 9.52 mm carries prepared with a soil load (mucin, BSA, and yeast extract per EPA MLB SOP MB-35-00). We treated seven carries with either ILPS undiluted and 3 carries with phosphate buffered saline (pH 7.4) for 10 minutes. We transferred and vortexed each carry in test tubes containing the 10 mls of specified broth (EPA MLB SOP MB-35-00). We cultured one ml of this supernate for treated and control carries. We recovered no colonies from the seven treated carries. The three untreated carries showed 7.21 7.1, and 7.2 $\log_{10}$ cultured CFUs.

Statistical Analysis

For both the Candida albicans and Candida auris we prepared Welch's "t" test for between groups with unequal variances. Both showed the difference between controls as significantly different from the treated groups (p<0.001; p<0.00057 specifically for C. auris).

Discussion

The unexpected rapidity the ILPS halts Candidal growth for both albicans and auris species, strongly suggests a rapid binding and to the external cell membrane and disruption of cellular metabolism. But cell death akin to the effects of hypochlorite solutions does not occur within mammalian skin cells washed with these soaps daily as a cosmetic confection. Nor does it appear to happen to people who consume isomerized linoleic acid in the form of diglycerides and triglycerides as a nutritional supplement. The United States Food and Drug Administration as well as the EPA identifies these plant oils as GRAS (Generally Recognized As Safe).

These conjugated plant oils if anything have a healthy effect on gut and whole body homeostasis of mammals. Rumenic Acid falls within the class of over 20 different isomerized linoleates. This C18 polyunsaturated fat persists in the rumens contributes to the homeostasis the rumen's biome. We have shown that associating a potassium with this free fatty acid will also reduce the rapid growth of human pathogens. The meats of grass fed beef and other animals as well as the milk and milk products contain rumenic acid. Perhaps it provides the health benefits intuited to the dietary laws in religions limiting diet to only those animals with rumens. Isomerized linoleic fats have been in our diet for a long time, linked to the integrity of the gut microbiome.

One report identifies that ordinary concentrations of chemicals used in traditional cleaning of hospital rooms may not be sufficient to disinfect an environment contaminated with C. auris, eg. sodium hypochlorite.

Currently, we have few human friendly options to disinfect C. auris on surfaces or on human skin. We propose ILPS as a candidate for these activities. At least it may move the dialogue with our biome towards a more harmonious equilibrium within our body and environment by reducing skin burden of Candida species as well as environmental surfaces.

Example 6

The present example provides a case study using nebulized isomerized linoleic acid (LA) for outpatient treatment of symptomatic COVID-19. We report the resolution of COVID-19 related symptoms in 6 days in two moderate to high risk COVID-19 patients (CDC, 2020) treated with nebulized 0.5 ml 11 mM LA every 4 hours around the clock for 7 days in an outpatient setting. The lipid potassium salt LA is Generally Recognized As Safe (GRAS) by the FDA (Food Additive). We report that in vitro testing of LA 4.4-50.2 mM showed 99% kill-rate of COVID-19 in 2 minutes. Pulmonary symptoms resolved and pulse oximetry levels normalized within the same week of symptom onset, returning to their normal marital relations on day 6. This compares to the median recovery time of two weeks from onset of symptoms for mild, and three to six weeks for severe COVID-19 cases (WHO, 2020). LA with its capacity to provide an affordable intervention within a home environment deserves further study to determine if it reduces severity, length of symptoms, and complications of COVID-19.

Severe acute respiratory syndrome coronavirus 2 (SARS-COV-2) is the virus that causes the disease, COVID-19. There is currently no effective therapy available for patients diagnosed with COVID-19 in the outpatient setting (Wu et al., 2020). Socioeconomic factors need to be assessed along with comorbidity diagnoses when evaluating the risk for COVID-19 patients. The current protocol that follows a positive COVID-19 test, in the absence of significant hypoxemia, is to monitor symptoms in isolation at home. However, this protocol can prove to be difficult for cohabitating households, especially when people are confined to shared small living spaces (Wu et al., 2020). For this couple, their home was less than 600 square feet, making effective social distancing impossible. Both the husband and wife had multiple morbidity factors known to increase the likelihood of symptom progression, severity, and death from COVID-19.

Virology Methods
Virus, Media, and Cells

SARS-COV-2 virus stocks were prepared by growing virus in Vero 76 cells. Test media used was MEM supplemented with 2% FBS and 50 mg/mL gentamicin.
Virucidal Assay, Kill-Rate Equivalency to 63% Ethanol LA 444 mM was serially diluted 2-fold in water for final test concentrations of 90% (339 mM), 45% (199.8 mM), 22.5% (99.9 mM), and 11.3% (50.2 mM). SARS-COV-2 virus stock was added to triplicate tubes and media only was added to one tube of each prepared concentration to serve as toxicity controls. Ethanol was tested in parallel as a positive control and water only to serve as the virus control.

Compound and virus were incubated at room temperature for a contact time of 2 minutes. Following the contact period, the solutions were neutralized by a 1/10 dilution in test media containing 10% FBS.

The experiment was repeated in the same way as described above testing lower concentrations of 11.3% (50.2 mM), 1% (4.4 mM), 0.5% (2.2 mM), and 0.25% (1.1 mM).
Virus Quantification Neutralized samples were combined for quantification for the average of triplicate tests. Samples were serially diluted using eight half-log dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus. All plates were incubated at 37±2° C., 5% CO2.

On day 6 post-infection plates were scored for presence or absence of viral cytopathic effect (CPE). The Reed-Muench method was used to determine end-point titers (50% cell culture infectious dose, CCID50) of the samples, and the log reduction value (LRV) of the compound compared to the negative (water) control was calculated.
Controls Virus controls were tested in water and the reduction of virus in test wells compared to virus controls was calculated as the log reduction value (LRV). Toxicity controls were tested with media not containing virus to see if the samples were toxic to cells.

Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.
Virucidal Assay Results Virus titers and LRV of LA against SARS-COV-2 are shown in Table 1. Full toxicity was observed in the 1/10 and 1/100 dilutions for the 22.5%-90% samples, and in the 1/10 dilution of 11.3%. Because of this toxicity, presence of virus could not be ruled out in those wells therefore the limit of detection for the 22.5%-90% tests was 2.7 and for the 11.3% was 1.7 log CCID50 of virus per 0.1 mL.

Virucidal activity was exhibited when 11.3% (50.2 mM) was incubated with virus for 2 minutes, reducing virus from 3.5 log CCID50 per 0.1 mL in virus controls to below the limit of detection of 1.7 logs (>98%). Higher concentration from 22.5%-90% also reduced virus below the limit of detection of 2.7 log CCID50 per 0.1 mL (>80%). This was identical to 63% ethanol kill-rate.

In the second experiment testing LA at lower concentrations, the 11.3% (50.2 mM) sample again reduced virus from 3.7 log CCID50 per 0.1 mL below the limit of detection (<1.7 logs, >99%) and the 1% (4.4 mM) sample reduced virus titer to 1.7 log CCID50 per 0.1 mL (99%). The 0.5% and 0.25% samples did not reduce virus by >1 log.

Neutralization controls demonstrated that residual sample did not inhibit virus growth and detection in the endpoint titer assays in wells that did not have cytotoxicity. Positive controls performed as expected, though ethanol was also toxic to cells in the 1/10 dilution, limiting the detection of virus to <1.7 log CCID50 per 0.1 mL.

TABLE 7

| Concentration | Reduction in Virus Titer[a] | LRV[b] |
|---|---|---|
| LA 90% (399.6 mM) | <2.7 | >08 |
| LA 45% (199.8 mM) | <2.7 | >08 |
| LA 22.5% (99.9 mM) | <2.7 | >08 |
| LA 11.3% (50.2 mM) | <1.7 | >1.8 |
| Ethanol 63% | <1.7 | >1.8 |
| Virus Control | n/a | |

[a]Log10 CCID50of virus per 0.1 mL
[b]LRV (log reduction value) is the reduction of virus compared to the virus control Table 7 shows virucidal efficacy of LA 444 mM against SARS-COV-2 after incubation with virus for 2 minutes at 22±2° C.

TABLE 8

| Concentration | Reduction in Virus Titer[a] | LRV[b] |
|---|---|---|
| LA 11.3% (50.2 mM) | <1.7 | >2.0 |
| LA 1% (4.4 mM) | <1.7 | >2.0 |
| LA 0.5% (99.9 mM) | <3.5 | >0.2 |
| LA 0.25% (50.2 mM | <3.3 | >0.4 |
| Ethanol 63% | <1.7 | >2.0 |
| Virus Control | n/a | |

[a]$Log_{10}$ CCID50of virus per 0.1 mL
[b]LRV (log reduction value) is the reduction of virus compared to the virus control Table 8 shows replicate 1-Virucidal efficacy of LA 444 mM against SARS-CoV-2 after incubation with virus for 2 minutes at 22±2° C.

Case Study Description

After informed consent of the risks and potential benefits, we nebulized 0.56 ml 11 mM LA every 4 hours to treat two COVID-19 patients. The initial treatment of the husband began after two days of symptoms and the wife began treatment after her first day symptoms. Treatment observations of these two cohabiting patients occurred in their home to alter the likely course of clinical deterioration given their co-morbidities.

Husband's Clinical Course

A 63-year old African American male presented with a two-day history of nasal congestion, cough, loss of taste and smell, mild dyspnea, and a mild hoarse voice. During the treatment timeline he also reported chest pain. The symptoms began 6 days post an Emergency Department (ED) visit for an unrelated problem where he tested positive for COVID-19.

He had no respiratory symptoms, or symptoms of fever or chills. His vitals included heart rate of 88 BP 148/80, oxygen saturation 97%, and a respiratory rate of 20. The patient was discharged from the ED and told to isolate at home.

He was living with his wife in a confined living space (less than 600 square feet). His wife was advised to quarantine away from him in the same home while he isolated which was clearly not possible. She developed symptoms as noted under Wife's Clinical Course.

Husband's Past Medical history: Non-Insulin Dependent Diabetes Mellitus, poorly controlled hypertension, obesity (Basal Metabolic Index 36.5), diverticulosis, Gastro-Esophageal Reflux Disease, and osteoarthritis.

During the Husband's pre-treatment exam, he showed no signs of respiratory distress. However, oxygen saturation measured 94%.

He was treated with 0.56 ml 11 mM nebulized LA every 4 hours, around the clock for 7 days. Oxygen saturation levels were recorded by the patient using a pulse oximeter. The initial and final evaluation was conducted as a home visit. All other evaluations were conducted by telephone. The treatment timeline starts the day after the initial home visit.

Day 1: he reported a total loss of taste and smell and mild chest pain. He also reported absence of dyspnea early that day and improved cough. His oxygen saturation measured 98% (up from 94%).

Day 2: he reported intermittent taste and smell through day 4. His chest pain resolved. He also reported infrequent loose bowel movements which improved and resolved over the following 3 days. He described no dyspnea. His oxygen saturation measured 97%.

Day 3: he reported a return of mild dyspnea. His oxygen saturation measured 95%.

Day 4: he reported dyspnea improvement. His oxygen saturation measured between 95-98%.

Day 5: he reported that his sense of taste and smell was close to normal. He also reported that his cough had resolved and he had minimal dyspnea. His oxygen saturation measured 97%.

Day 6: no reported symptoms. His oxygen saturation measured 97%.

Day 7: no reported symptoms. His oxygen saturation measured 98%.

This completed his 7-day treatment of nebulized LA.

Wife's Clinical Course

This 56-year old African American female presented with a 1-day history of nasal congestion, cough, and loss of taste and smell. On the date of presentation, she also reported having symptoms of minimal wheezing and dyspnea.

She had been tested for SARS-COV-2 due to being a close contact of her husband. She was tested by nasal swab twice: 3 days prior and again 1 day prior to the onset of symptoms. Both test results came back negative. She was treated as a probable positive after informed consent.

Wife's Past Medical History: chronic asthma, hypertension, hypothyroidism, pre-diabetes, and obesity (BMI 43.4).

After informed consent of the risks and potential benefits, we nebulized 0.56 ml 11 mM LA every 4 hours around the clock for 7 days. Before beginning treatment, she showed no signs of respiratory distress. Her initial oxygen saturation measured 96%.

Oxygen saturation levels were recorded by the patient using a pulse oximeter. The initial and final evaluation was conducted as a home visit. All other evaluations were conducted by telephone. The treatment timeline starts the day after the initial home visit.

Day 1: she reported loss of taste and smell and fatigue. Her wheezing had improved. She reported no dyspnea. Oxygen saturation measured 95%.

Day 2: she reported mild wheezing and dyspnea. Her oxygen saturation measured 94%. An additional treatment of an Albuterol nebulizer and Methylprednisolone Dosepak was started for her asthma exacerbation. When starting nebulized Albuterol, this patient inadvertently discontinued the nebulized LA because she misunderstood instructions. This cessation of nebulized LA was not reported to the treating physician until Day 4.

Day 3: she reported improved loss of taste and smell and cough. Dyspnea worsened. Oxygen saturation measured 98%

Day 4: she reported that the loss of taste and smell improved. She also reported mild wheezing and cough. Oxygen saturation measured 95%. The patient reported the Albuterol nebulizer aggravated dyspnea symptoms. Because of her complaint, the Albuterol nebulizer was discontinued. Nebulized LA treatment was started again.

Day 5: she reported no loss of taste and smell. Minimal cough, wheeze, and dyspnea. Oxygen saturation measured 96%

Day 6: no reported symptoms. Oxygen saturation measured 98%.

Day 7: no reported symptoms. Oxygen saturation measured 98%.

This completed her 7-day treatment of nebulized LA.

This husband-wife returned to normal marital relations on day 6.

Discussion

Virological studies demonstrate that LA 4.4-50.2 mM kills 99% of virus (Covid-19) within 2 minutes. As this continues to be a GRAS ingredient as determined by the FDA, nebulizing the LA posed little potential harm in the context of offering the potential results born out in this report.

This report reviews the clinical progress of a husband and wife with COVID-19 symptoms treated with nebulized LA. Both patients had multiple high-risk morbidities for progression of symptoms including the presence of dyspnea (Li, L. et al., 2020), mild hypoxia (Cecconi et al., 2020; Li, X. et al., 2020) and chest pain (Liang et al., 2020) during the course of illness. Most high-risk patients progressing to death have comorbidities of age (>50, obesity, hypertension, diabetes, pulmonary and other systemic diseases) (Buckner et al., 2020; Sharma et al., 2020). Treatment with nebulized LA led to a complete reversal of symptoms and hypoxemia by day 6 of treatment for both patients.

The husband showed rapid reversal of mild hypoxemia and had no symptoms relating to his COVID-19 diagnoses following day 5 of treatment with nebulized LA.

The wife followed a course that was complicated by her underlying asthma. On day 2 of treatment she was noted to have an increase in wheeze and dyspnea. Her pulse oximeter recorded a worsening of hypoxia. She was started on standard therapy for asthma with an oral steroid and nebulized Albuterol. On the same day she mistakenly discontinued the nebulized LA without the treating physician's knowledge. The mistake was not discovered until day 4 of treatment when she reported an increase in dyspnea symptoms after nebulization treatments. When asked which treatment was causing side effects, she reported only using Albuterol on the second and third days. Nebulized Albuterol was discontinued and she was started back on nebulized LA through day 7. She was asymptomatic by day 6.

Both patients reported no side effects to nebulized LA. They noted a generalized feeling of improvement in being able to breathe normally after treatments. Length of illness in mild cases in China have been reported with a median length of symptoms of 2 weeks (WHO, 2020). The two patients in this report had a mild to moderate presentation and their symptoms lasted five days. Both patients were assessed as mild to moderate because of symptoms of dyspnea, chest pain, and mild hypoxemia. Both have remained asymptomatic for COVID-19 related symptoms after an additional 3 weeks, which is the time this paper was submitted for publication.

Both husband and wife had sought medical care without health insurance. They had concerns that this barrier would limit their access to healthcare. In in the context of the COVID-19 pandemic, the decision to treat with nebulized LA was weighed. After evaluating the grim prospect that the absence of an early intervention could be dire and the use of LA for nebulizing posed minimal risk, the patients and physician decided to move forward with this treatment. The simple fact of availability and its immediate clinical response suggests an affordable potentially effective intervention that can provide widespread implementation. This low-cost intervention does not require hospital resources, rather it establishes an early intervention that may prevent later complications caused by late stage heightened immune response (Upadhay et al., 2020). This easily implemented outpatient nebulizer treatment needs further study to evaluate if it will reduce ICU burden. Most clinical research focuses on inpatient care (Park et al., 2020). The focus that restricts therapies within hospital settings could harm the opportunity to discover effective outpatient therapies (Park et al., 2020). In order to mitigate the suffering brought on by this pandemic, there needs to be a low-cost and easily accessible and effective intervention that prevents transmission, disease severity, and late stage complications.

A recent article published in the journal Science, researchers from the UK, Germany, and Switzerland discovered that LA's tertiary structure provides 3 docking points for the SARSCOV-2 spike protein, thus preventing viral binding to the ACE2R (C. Toelzer et al., 2020) The structure of SARS-COV-2 and it's trimer spike protein binding to the ACE2R initiates the invasion into the host cells and the opportunity to cause disease (C. Toelzer et al., 2020). Both animal and clinical studies concerning SARS-COV-2 indicate that the virus enters the mucin producing cells lining the nose by binding ACE2R (Mason, 2020; Sungnak et al., 2020). The hijacking of the goblet cells does not lead to cell death, allowing the virus to replicate and overwhelm the nasal and pulmonary epithelium. SARS-COV-2 can cause a heightened immune/inflammatory response and the upregulation of ACE2R with the production of interferon (C. Toelzer et al., 2020). As the virus invades deeper into the lung tissue, it kills the alveolar epithelial type II cells that also contain ACE2R and can be followed by severe pulmonary cytokine storm (Mason, 2020; Sungnak et al., 2020).

Early antiviral intervention before peak viral transcription is desirable. LA binding to receptor binding domains of SARS-COV-2 stabilizes the spike glycoprotein conformation (C. Toelzer et al., 2020). This has been shown to reduce the SARS-COV-2 contact with the ACE2R in vitro (C. Toelzer et al., 2020).

LA is readily available commercially as a nasal oral wash (Changaris & Carenbaurer, 2020). LA 4.4-50.2 mM showed 99% kill-rate in 2 minutes of SARS-Cov-2 during in vitro studies at Utah State University, Institute for Antiviral Research. This is identical to the efficacy of 63% ethanol.

The oropharynx and nasopharynx serve as major sites of SARS-COV-2 replication during the early stages of infection. Topical oral washes, including Povodine Iodine and Chlorhexidine are currently being studied to reduce upper respiratory viral load, thus potentially reducing the opportunity for transmission and infection (Meister et al., 2020). None of these have been proposed for nebulized therapies to treat pulmonary progression of SARS-COV-2. They also have serious limitations with respect to general use, safety, and environmental hazards.

Recently, nasal administration of 0.5 ml of a solution topical dimeric lipopeptide has prevented the transmission of SARS-COV-2 in ferrets. A daily nasal spray was shown to be completely effective in preventing transmission of SARS-COV-2 in ferrets (de Vries et al., 2020). This provides support to nasopharyngeal administration of anti-virals to treat and/or prevent transmission of SARS-COV-2.

Nasal and oral washes with LA need further study in humans to determine if transmission of infection is prevented. LA can be used not only as an oral and nasal wash, but also via nebulization which provides added potential therapeutic application for this product.

LA is consumed by mouth in gram quantities as a nutritional supplement/food additive accepted by the FDA (2009) as Generally Recognized as Safe. Nebulized LA was well tolerated by both patients. Both patients reported no side effects and reported improved breathing after treatments and have remained asymptomatic.

Conclusion

Nebulized LA altered the likely clinical course of COVID-19 in two cohabiting patients living in close proximity, unable to socially distance for economic reasons. The couple returned to normal marital relations and good health by day 6 of nebulizer therapy. This remarkably safe lipid LA warrants further testing as a candidate to treat COVID-19. It appears to provide an inexpensive and simple home intervention that can be started following the onset of symptoms while in isolation at home. This report suggests that this treatment is well tolerated. LA has 99% virucidal activity in vitro at 4.4-50.2 mM, as effective as 63% ethanol. This report suggests that this treatment is well tolerated.

Nebulization provides a simple cost-effect practical delivery of LA to the site of viral replication in cases with pulmonary symptoms. Further studies are needed to clarify its potential reduction of length and severity of illness, and also reduction of hospitalization and complication rates. The relative simplicity, minimal cost, and presence of the lipid LA in normal human physiology warrants support for further study.

Example 7

The present example shows symptom duration shortened by early initiation of nebulized isomerized linoleic acid (LA) for outpatient treatment of COVID-19. With a total of 6 patients, albeit a small number, we find a statistically significant correlation between 'when beginning nebulizing treatment with LA' and the 'length of reported COVID related symptoms' ($p<0.01$; $r=0.965$). We report the clinical course of four COVID-19 cases, 2 probable cases, and 2 close contacts treated with nebulized Isomerized Linoleic Acid (LA). Comorbidity ranged from none to high risk. No side effects were reported by this group of patients. Isomerized LA was completely effective in the small sample of close contacts. Early treatment onset shortened the duration of symptoms. We define symptom duration as the total length of symptoms that were reported during the course of illness. All patients reported a total resolution of symptoms after treatment, except for one who started nebulized LA 4 days after onset of symptoms of infection, who reported some lingering fatigue. The case study findings could pose a potential timeline for future research into when nebulized LA treatment would be most effective. Complications of COVID-19 appeared to be affected by early onset of treatment. Since global case counts and deaths attributed to COVID-19 are continuing to rise, there needs to be an effective, low cost outpatient therapeutic available. Nebulized LA provides the opportunity for just that, a safe, low cost, and effective option for outpatient COVID-19 treatment. We hope this case study will prompt further and much needed research into COVID-19 outpatient treatment.

As we wait for an effective vaccine, global case counts, hospitalizations, and deaths continue to rise. This burdens hospital ICU systems and the number of people affected daily by COVID-19. An early intervention treatment could greatly reduce this burden and the real-time suffering of individuals affected by COVID-19. Recently in JAMA, co-author Anthony Fouchi states: "Yet, there is a noteworthy absence of treatments proven to be efficacious for patients with early or mild infection. Immediate benefits of such treatments include improvement of patient outcomes and prevention of hospitalizations . . . Outpatient treatments for COVID-19, coupled with an effective vaccine, would have significant implications for the ability to end this pandemic. (Kim P S et al., 2020)"

Recently we reported that in vitro virological testing of LA 4.4-50.2 mM showed 99% kill-rate of COVID-19 in 2 minutes (Jonsson, et al 2020). In addition, we reported on the first 2 patients successfully treated with nebulized LA, with reduced duration for resolution of symptoms and no reported side effect at follow up. This treatment appeared to reduce symptom severity and length of symptoms in 2 mild to moderately symptomatic patients who were at moderate to high risk (Jonsson et al., 2020).

This case report provides evidence that nebulized LA is safe and tolerated by individuals who have been diagnosed with and exposed to COVID-19. This case report serves to show a reduction of symptom duration when treatment was started early. In 2009 FDA approved LA as generally recognized as safe (GRAS) for human consumption. This case report provides ongoing support of the safety of this product following the nebulized route of administration.

Review of Previously Reported Virucidal Assay Results (Jonsson et al., 2020)

Virus titers and LRV of LA against SARS-COV-2 are shown in Table 1. Full toxicity was observed in the 1/10 and 1/100 dilutions for the 22.5%-90% samples, and in the 1/10 dilution of 11.3%. Because of this toxicity, presence of virus could not be ruled out in those wells therefore the limit of detection for the 22.5%-90% tests was 2.7 and for the 11.3% was 1.7 log CCID50 of virus per 0.1 mL.

Virucidal activity was exhibited when 11.3% (50.2 mM) was incubated with virus for 2 minutes, reducing virus from 3.5 log CCID50 per 0.1 mL in virus controls to below the limit of detection of 1.7 logs (>98%). Higher concentration from 22.5%-90% also reduced virus below the limit of detection of 2.7 log CCID50 per 0.1 mL (>80%). This was identical to 63% ethanol kill-rate. In the second experiment testing LA at lower concentrations, the 11.3% (50.2 mM) sample again reduced virus from 3.7 log CCID50 per 0.1 mL below the limit of detection (<1.7 logs, >99%) and the 1% (4.4 mM) sample reduced virus titer to 1.7 log CCID50 per 0.1 mL (99%). The 0.5% and 0.25% samples did not reduce virus by >1 log.

Neutralization controls demonstrated that residual sample did not inhibit virus growth and detection in the endpoint titer assays in wells that did not have cytotoxicity. Positive controls performed as expected, though ethanol was also toxic to cells in the 1/10 dilution, limiting the detection of virus to <1.7 log CCID50 per 0.1 mL.

TABLE 9

| Concentration | Reduction in Virus Titer[a] | LRV[b] |
|---|---|---|
| LA 11.3% (50.2 mM) | <1.7 | >2.0 |
| LA 1% (4.4 mM) | <1.7 | >2.0 |
| LA 0.5% (99.9 mM) | <3.5 | >0.2 |
| LA 0.25% (50.2 mM | <3.3 | >0.4 |
| Ethanol 63% | <1.7 | >2.0 |
| Virus Control | n/a | |

[a]$Log_{10}$ CCID50 of virus per 0.1 mL
[b]LRV (log reduction value) is the reduction of virus compared to the virus control Case Study Description Table 9 shows virucidal efficacy of LA 444 mM against SARS-COV-2 after incubation with virus for 2 minutes at 22±2° C.

Four lab confirmed COVID-19 cases, 2 probable cases, and 2 close contacts of confirmed COVID-19 cases were nebulized 0.56 ml 11 mM LA (Table 2). Treatment with LA was started after patients were assessed by their primary physician. Patients presented at different points in their COVID-19 infection. Onset of treatment ranged from asymptomatic to 9 days into the symptom course. Two close contacts with cases were treated. They were asymptomatic. Two close contacts with COVID-19 cases were also nebulized using 0.56 ml 11 mM LA every 4 hours. One patient was treated for 7 days, and the other for 10 days. Both of these patients tolerated treatment without side effects and neither developed symptoms of COVID-19.

TABLE 10

| | Duration of Symptoms Before Treatment (in days) | Total Duration of Symptoms (in days) | COVID-19 Complications | Age/Sex/Comorbidities |
|---|---|---|---|---|
| Cases | | | | |
| 1 | 0 | 0 | none | 64/F/none |
| 2 | 2 | 7 | none | 63/M/NIDDM, Hypertension, Obesity |
| 3 | 4 | 16 | ED visit, steroid, oxygen | 56/M/Hx recurrent DVT. Asthma, Antiphospholipid syndrome. |
| 4 | 9 | 23 | ED visit, 1 overnight hospitalization,, steroid, oxygen | 74/F/Mild Dementia, Coronary Artery Disease, Carotid Artery Stenosis w history of CVA, Prediabetes. |
| Probable Cases | | | | |
| 1 | 1 | 6 | Steroid for asthma | 56/F/asthma, hypertension, hypothyroidism, pre-diabetes, and obesity |
| 2 | 3 | 10 | none | 49/F/none |
| Close Contacts | | | | |
| 1 | 0 | 0 | none | 59/M/Hypertension |
| 2 | 0 | 0 | none | 66/M/NIDDM, Obesity |

Table 10 exhibits of cases and presumptive cases of Covid-19 showing onset of treatment with nebulized LA and length of symptoms.

1: Is a 64 year old Caucasian female. She has the following comorbidities: Obesity (BMI 34.8). She tested routinely 3 days following out of state travel to visit family. She was treated with nebulized 0.56 ml 11 mM LA every 4 hours for 7 days. She tolerated the Cases nebulization without side effects and remained asymptomatic for the duration of her isolation period.

2: Is a 63 year old African American male with a positive test through the ED 6 days earlier when he presented with an unrelated problem. His comorbidity included NIDDM, poorly controlled hypertension, obesity (BMI 36.5), diverticulosis, GERD, and also osteoarthritis. He presented with a two day history of nasal congestion, cough, loss of taste and smell, mild dyspnea, and a mild hoarse voice. He was treated with nebulized 0.56 ml 11 mM LA every 4 hours for 7 days. He was mildly hypoxic with pulse oximetry measuring 94%. During the treatment timeline he also reported chest pain. He followed an uncomplicated course and was symptom free after 7 days from symptom onset.

3: Is a 56 year old Caucasian male with a prior history of recurrent DVT, and comorbidities including antiphospholipid syndrome, asthma, overweight (BMI 27.6). His symptoms started with severe headache and myalgia. The following day he was seen through urgent care where he tested positive for COVID-19 and was told to isolate. He was evaluated on day 3 following symptom onset via Telehealth by his primary care physician. He was experiencing significant symptoms of myalgia and also chills. During this visit he had a syncopal spell and was taken to the ED. His workup included normal labs and a CT chest angiogram. He was advised to return home in isolation. On day 4, he started on 0.56 ml 11 mM LA via nebulization every 4 hours. He continued to experience moderate symptoms including fatigue and intermittent chills. On day 10 his oxygen levels measured 91-92%, Methylprednisolone was prescribed. Symptoms including myalgia, fatigue and chills improved. Oxygen levels remained low measuring 88-91% on room air and low flow oxygen 1 Liter/minute via nasal cannula was provided from day 12 through day 14. On day 14 supplemental oxygen was discontinued with oximetry measuring 94% on room air. On day 16 from symptom onset he reported a total resolution of initial symptoms. Nebulized LA was discontinued on day 16, after 12 days of nebulization. He described no significant side effects to this treatment. He was the only case who reported some lingering fatigue after treatment was discontinued. However, he was still able to return to work on a reduced work hour schedule the day after finishing treatment.

4: Is a 74 year old Caucasian female with multiple comorbidities. She has a history of mild dementia, mixed anxiety depression, CAD, Carotid artery stenosis with a history of CVA, and prediabetes. She had a normal BMI 21.2. She was living in independent living and was sent to the ED because staff at her facility were concerned that she appeared weak. Her only complaints were fatigue and weakness. It is unclear as to when her symptoms had started. COVID-19 test was positive. Vitals included blood pressure 156/66, heart rate 60, O2 saturation 91%. Respiratory rate 18. Temperature 99.9°. Blood work was normal. Chest x-ray was significant for left upper lobe pneumonia in a patchy peripheral distribution consistent with COVID-19. Nebulized LA treatments were attempted at home but were unsuccessful because of inadequate support available to her in independent living. She was sent by staff to the ED on day 6 because they were concerned that she continued to appear weak. She was admitted overnight because of hypoxia secondary to COVID-19 pneumonia. Vitals in the ED included HR 68, BP 146/69. RR 20, Temp 99.4. Oxygen saturation 86%. She was treated with supplemental oxygen and also steroids. She showed no clinical signs of respiratory distress and was sent back to independent living the following day using supplemental oxygen via nasal cannula at a flow of 2 liters/min. 0.56 ml 11 mM LA via nebulization was started on day 9 when staffing was able to support this home treatment. On day 9 she received two treatments, and then her treatments were increased to 4 times a day. She received treatments through day 23, for a total of 14 days. On day 25, supplemental oxygen was discontinued with oxygen levels measured between 96 and 98%. She reported no side effects to the nebulized LA treatments.

Probable Cases

1: Is a 56 year old African American female with the following comorbidities: asthma, hypertension, hypothyroidism, pre-diabetes, and obesity (BMI 43.4). She presented with a 1 day history of nasal congestion, cough, and loss of taste and smell, wheezing and dyspnea. She was a cohabitant with a case living in a confined home living area. She was tested twice: 3 days prior and again 1 day prior to the onset of symptoms. In retrospect, testing was performed too early. Both test results came back negative. She was treated as a probable positive. She was treated with nebulized 0.56 ml 11 mM LA every 4 hours for 7 days. Her clinical course was complicated by an exacerbation of her asthma and also side effects to nebulized albuterol. She was treated with methylprednisolone. She was symptom free by day 7. She had no side effects to nebulization LA.

2: Is a 49 year old Caucasian female without comorbidities. Her BMI was 22.1, She developed symptoms 1 day after her husband's symptom onset. He tested positive for COVID-19 on the day of her symptom onset. She had negative testing performed 6 days post symptoms onset. This was 3 days after starting her treatment which could have affected the results of her COVID-19 test. She was treated with nebulized 0.56 ml 11 mM LA every 4 hours for 10 days. Her symptoms included moderate nasal congestion, and also mild loss of smell, chest pressure, headache and fatigue. Her clinical course was uncomplicated and her symptoms had all resolved after 10 days.

Close Contacts

1: Is a 59 year old Caucasian man. He had the following comorbidity: Hypertension. He was exposed during a dental procedure 5 days prior. His dentist tested positive and he received a call to quarantine and monitor for symptoms. He was treated with nebulized 0.56 ml 11 mM LA 4 times a day for 10 days. He did not develop symptoms of Covid-19 infection. He reported no side effects to isomerized LA.

2: Is a 66 year old Caucasian man. He had the following comorbidity: NIDDM, OSA, Obesity (BMI 40.0). He was exposed to his cohabiting wife who was a COVID-19 case. He was treated with nebulized 0.56 ml 11 mM LA every 4 hours for 7 days. He did not develop symptoms of Covid-19 infection. He reported no side effects to isomerized LA.

FIG. 3 shows the total symptom duration which is affected by the time nebulized LA treatment is started after symptom onset. The total duration of COVID-19 symptoms is reduced the earlier in their illness that patients are treated with nebulized LA.

Statistical Analysis Correlating when Treatment Began with Respect to COVID-19 Symptom Onset with the Length of Reported Symptoms FIG. 4 shows a correlation between 'when beginning treatment' and 'length of reported COVID-19 related symptoms' ($p<0.01$; $r=0.965$). We used a Pearson Linear Correlation Test with 4 degrees of freedom with the information defined in FIG. 3.

Discussion

There has been an absence of effective outpatient therapies during the early stages of COVID-19. (Kim P S et al., 2020). An effective outpatient treatment may provide the largest impact on the COVID-19 pandemic (Park et al., 2020).

As recently reported in the journal Science, in vitro studies showed that linoleic acid disrupts the tripeptide S1 sufficiently to block cell entry (Toelzer et al., 2020). LA is readily available commercially as a nasal oral wash (Changaris & Carenbaurer, 2020). LA 4.4-50.2 mM showed 99% kill-rate in 2 minutes of SARS-Cov-2 during in vitro studies at Utah State University, Institute for Antiviral Research. This is identical to the efficacy of 63% ethanol (Jonsson et al., 2020).

This case report reviews the clinical progress of 8 patients treated with nebulized LA. We have provided additional evidence that this intervention appears to be safe. None of the eight patients reported any side effects while nebulizing with LA.

Nebulized LA may be an effective prevention strategy for those who have been exposed to the virus. Two patients with significant exposure to COVID-19 were nebulized. No side effects were reported and neither reported symptoms of infection.

FIGS. 3 and 4 provide strong evidence that early initiation of treatment for those infected provides the most benefit. All patients were free of all acute infection symptoms as reported in FIG. 1. Only one patient had lingering symptoms of fatigue measured on day 16 following onset of acute infection. His symptoms were mild and did not prevent return to work, albeit less than full schedule. Fatigue is a common persistent symptom in patients who have recovered from acute COVID-19 infection. In a study looking at 128 patients, over 50% of subjects had persistent symptoms of fatigue as measured 10 weeks (day 70) after initial symptoms of infection (Townsend et al., 2020).

The known in vitro virucidal activity of LA (Jonsson et al., 2020) provides a plausible explanation for this clinical observation since viral replication is highest during the early stages of infection before the host provides a targeted immunological response. The highest viral load is present before symptoms present, and subsequently decrease over time (Benefield et al., 2020). During the early stages of infection, the viral load is highest within the respiratory tract, and thus would be vulnerable to nebulized therapy (Wölfel et al., 2020). Nebulized LA provides a simple and safe intervention that can be administered within patients' homes. LA is inexpensive and sold without the need for a prescription and is generally recognized as safe (GRAS) for human consumption (FDA 2009). Nebulized LA is cheap to manufacture and affordable for the patient. This treatment does not discriminate due to access or opportunity.

Monoclonal antibodies have recently been approved under EUA (2020) for the treatment of mild to moderate COVID-19 patients in the outpatient setting who are not on oxygen and who are at risk for progressing to severe disease. Monoclonal antibody therapy faces potential obstacles to therapy including: high cost, the need for administration in an IV administration center, exposure to staff and patients within IV administration centers, and significant infusion related reactions. Monoclonal antibodies have also been associated with worsened outcomes when administered to hospital patients requiring oxygen (Goldstein R H & Walensky R P, 2020). On Nov. 11, 2020 JAMA published an assessment of the usefulness of monoclonal antibodies during this pandemic. As the authors reported in The Challenges Ahead With Monoclonal Antibodies From Authorization to Access: "The administration of monoclonal antibodies will further tax outpatient clinics and challenge the ability of clinicians and health care centers to provide adequate and equitable access. The currently studied monoclonal antibody preparations require a 1-hour intravenous infusion. (Goldstein R H & Walensky R P, 2020)"

Effective outpatient solutions will most likely be born out of research in the outpatient setting (Park et al., 2020). Health care workers providing first contact with acute COVID-19 infections are best suited to evaluate such interventions since viral load is highest at this time. Antiviral therapies will have the most impact while viral load is still high. Non FDA approved interventions including EUA options need to be provided after adequate informed consent.

Conclusion

As worldwide COVID-19 cases increase, a safe and effective outpatient treatment, which will provide equal access to all socioeconomic groups is needed. LA has been approved by the FDA in 2009 and is generally recognized as safe (GRAS) for human consumption. In vitro virological testing of LA 4.4-50.2 mM showed 99% kill-rate of COVID-19 in 2 minutes (Jonsson et al., 2020). Nebulization provides a simple cost-effect practical delivery of LA to the site of viral replication in cases with pulmonary symptoms.

This report provides further support for the safety of nebulized LA where 8 patients were treated, reporting no side effects. It provides evidence that supports prevention of COVID-19 following significant exposure. In cases, early administration appears to provide the most benefit, with a reduction in the length and also severity of the clinical course. Nebulized LA also provides benefits including: low cost, and ease of administration in the home setting. As global cases continue to rise, this novel COVID-19 prevention and early outpatient treatment has potential to affect the current pandemic and invites further research.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The reference "Potassium Isomerized Linoleate Satisfies EPA MB-35-00 for Surface Disinfection of *Candida auris* (AR-0381) and *Candida albicans* (ATCC 10231)", by. David G Changaris and Anne L Carenbauer, *EC Microbiology* 17.10 (2021): 26-34. is hereby incorporated by reference. The incorporation of the publication may provide additional information relating to technical features of one or more embodiments. Words relating to the opinions and judgments of the author and not directly relating to the technical details of the description of the embodiments therein are not incorporated by reference.

One feature or aspect of an embodiment is believed at the time of the filing of this patent application to possibly reside broadly in a method of reducing the virulence of microbes in a human body comprising: applying to the human a solution to at least one of a mouth, the nasal cavities, the lungs, the eyes, or the vagina, or injecting a solution intravenously; wherein the applied or injected solution comprises a conjugated diene having a structure of R1-C=C—C=C—R2 in an amount effective for at least a log 2 kill of the microbes within two minutes of the applying or injecting of the solution.

Another feature or aspect of an embodiment is believed at the time of the filing of this patent application to possibly reside broadly in the method of reducing the virulence of microbes, wherein: R1 has an aliphatic chain; and R2 has a carbon chain and a carboxyl group or an acidic moiety.

Yet another feature or aspect of an embodiment is believed at the time of the filing of this patent application to possibly reside broadly in the method of reducing the virulence of microbes, wherein the solution further comprises at least one of water, amino acid, cations, and alcohol.

Still another feature or aspect of an embodiment is believed at the time of the filing of this patent application to possibly reside broadly in the method of reducing the virulence of microbes, wherein the solution comprises cations at least at a substantially molar equivalent to the conjugated diene in the solution.

A further feature or aspect of an embodiment is believed at the time of the filing of this patent application to possibly reside broadly in the method of reducing the virulence of microbes, wherein the cations have at least one of lithium, sodium, potassium, and rubidium.

Another feature or aspect of an embodiment is believed at the time of the filing of this patent application to possibly reside broadly in the method of reducing the virulence of microbes, wherein the cations have sodium.

Yet another feature or aspect of an embodiment is believed at the time of the filing of this patent application to possibly reside broadly in the method of reducing the virulence of microbes, wherein the cations have potassium.

Still another feature or aspect of an embodiment is believed at the time of the filing of this patent application to possibly reside broadly in the method of reducing the virulence of microbes, wherein the solution comprises the cations at a molar ratio of the cations to the conjugated diene between about 1:1 and 5:1.

A further feature or aspect of an embodiment is believed at the time of the filing of this patent application to possibly reside broadly in the method of reducing the virulence of microbes, wherein the conjugated diene has up to 40 carbons.

Another feature or aspect of an embodiment is believed at the time of the filing of this patent application to possibly reside broadly in the method of reducing the virulence of microbes, wherein the conjugated diene has between 8 carbons and 30 carbons.

Yet another feature or aspect of an embodiment is believed at the time of the filing of this patent application to possibly reside broadly in the method of reducing the virulence of microbes, wherein the aliphatic chain in R1 has between 3 carbons and 13 carbons.

One feature or aspect of an embodiment is believed at the time of the filing of this patent application to possibly reside broadly in the method of reducing the virulence of microbes, wherein the aliphatic chain in R1 has between 6 carbons and 9 carbons.

Another feature or aspect of an embodiment is believed at the time of the filing of this patent application to possibly reside broadly in the method of reducing the virulence of microbes, wherein the carbon chain in R2 has between 2 carbons and 15 carbons.

Yet another feature or aspect of an embodiment is believed at the time of the filing of this patent application to possibly reside broadly in the method of reducing the virulence of microbes, wherein the carbon chain in R2 has between 4 carbons and 5 carbons.

Still another feature or aspect of an embodiment is believed at the time of the filing of this patent application to possibly reside broadly in the method of reducing the virulence of microbes, wherein the solution has a concentration of the conjugated diene between 0.1 millimolar and 500 millimolar.

A further feature or aspect of an embodiment is believed at the time of the filing of this patent application to possibly reside broadly in the method of reducing the virulence of microbes, wherein the solution has a concentration of the conjugated diene between 0.2 millimolar and 60 millimolar.

Another feature or aspect of an embodiment is believed at the time of the filing of this patent application to possibly reside broadly in the method of reducing the virulence of microbes, wherein the microbes are selected from the group consisting of gram positive bacteria, gram negative bacteria, virus, fungus, yeast, and combinations thereof.

Yet another feature or aspect of an embodiment is believed at the time of the filing of this patent application to possibly reside broadly in the method of reducing the virulence of microbes, wherein the microbes have a microbial surface containing at least one region having greater than 10% of histidine, proline, tryptophan, phenylalanine, lactones, or hydrophobic moieties.

Still another feature or aspect of an embodiment is believed at the time of the filing of this patent application to possibly reside broadly in the method of reducing the virulence of microbes, wherein the microbes have at least 6% amino acids or chemical structures, wherein a solution having 6% of the amino acids or chemical structures and 8% of the conjugated diene yields at least a two log-reduction in a viscosity of the solution.

A further feature or aspect of an embodiment is believed at the time of the filing of this patent application to possibly reside broadly in a method of sanitizing or disinfecting a surface, area, object, or porous or non porous material comprising: applying an effective amount of a conjugated diene having a structure of R1-C=C—C=C—R2 to the surface, the area, the object, or the porous or non-porous material, wherein a solution comprises the effective amount of the conjugated diene for at least a 2 log kill of microbes within two minutes of the applying of the solution.

The present disclosure is not to be limited in terms of the particular examples or embodiments described in this application, which are intended as illustrations of various aspects. Many modifications and variations can be made without departing from its spirit and scope, as will be apparent to those skilled in the art. Functionally equivalent materials, equipment, methods, and apparatuses within the scope of the disclosure, in addition to those enumerated herein, will be apparent to those skilled in the art from the foregoing descriptions. Such modifications and variations are intended to fall within the scope of the appended claims.

The invention claimed is:

1. A method of reducing the virulence of microbes or the microbes of diseases thereof in a human body comprising:

applying to the human a solution to at least one of a mouth, the nasal cavities, the lungs, the eyes, or the vagina, or injecting a solution intravenously;

wherein the applied or injected solution comprises a conjugated diene having a structure of R1-C=C—C=C—R2 in an amount effective for at least a log 2 kill of the microbes or diseases thereof within two minutes of the applying or injecting of the solution;

wherein the microbes or diseases thereof are selected from the group consisting of *Candida auris, Candida albicans*, SARS-COV-2, COVID-19, and combinations thereof;

wherein R1 has between 6 carbons and 9 carbons and an aliphatic chain and R2 has between 4 carbons and 5 carbons, a carbon chain, and a carboxyl group.

2. The method of claim 1, wherein the solution further comprises one or more constituents selected from the group consisting of water, amino acid, cations, and alcohol.

3. The method of claim 1, wherein the solution further comprises cations at least at a molar equivalent to the conjugated diene in the solution.

4. The method of claim 3, wherein the cations are selected from the group consisting of lithium, sodium, potassium, rubidium, and combinations thereof.

5. The method of claim 4, wherein the cations have sodium.

6. The method of claim 4, wherein the cations have potassium.

7. The method of claim 3, wherein the solution comprises the cations at a molar ratio of the cations to the conjugated diene between about 1:1 and 5:1.

8. The method of claim 1, wherein the solution has a concentration of the conjugated diene between 0.1 millimolar and 500 millimolar.

9. The method of claim 8, wherein the solution has a concentration of the conjugated diene between 0.2 millimolar and 60 millimolar.

10. The method of claim 1, wherein the microbes or diseases thereof have a microbial surface containing at least one region having greater than 10% of histidine, proline, tryptophan, phenylalanine, lactones, or hydrophobic moieties.

11. The method of claim 1, wherein the microbes or diseases thereof have at least 6% amino acids or chemical structures, wherein a solution having 6% of the amino acids or chemical structures and 8% of the conjugated diene yields at least a two log-reduction in a viscosity of the solution.

12. A method of sanitizing or disinfecting a solid surface by reducing the virulence of microbes or the microbes of diseases thereof comprising:

applying an effective amount of a conjugated diene having a structure of R1-C=C—C=C—R2 to the solid surface;

wherein a solution comprises the effective amount of the conjugated diene for at least a 2 log kill of microbes or diseases thereof within two minutes of the applying of the solution;

wherein the microbes or diseases thereof are selected from the group consisting of *Candida auris, Candida albicans*, SARS-COV-2, COVID-19, and combinations thereof; and wherein R1 has between 6 carbons and 9 carbons and an aliphatic chain and R2 has between 4 carbons and 5 carbons, a carbon chain, and a carboxyl group.

* * * * *